(12) United States Patent
Amir

(10) Patent No.: US 9,012,160 B2
(45) Date of Patent: Apr. 21, 2015

(54) MONITORING SKIN METABOLISM PRODUCTS FOR EVALUATING BURN INJURY

(76) Inventor: Abraham Amir, Tel Mond (IL)

( * ) Notice: Subject to any disclaimer, the term of this patent is extended or adjusted under 35 U.S.C. 154(b) by 1126 days.

(21) Appl. No.: 12/999,378

(22) PCT Filed: Jun. 16, 2009

(86) PCT No.: PCT/IL2009/000598
§ 371 (c)(1),
(2), (4) Date: Mar. 2, 2011

(87) PCT Pub. No.: WO2009/153783
PCT Pub. Date: Dec. 23, 2009

(65) Prior Publication Data
US 2011/0151489 A1    Jun. 23, 2011

Related U.S. Application Data

(60) Provisional application No. 61/061,669, filed on Jun. 16, 2008.

(51) Int. Cl.
*G01N 33/53* (2006.01)
*G01N 31/00* (2006.01)
*G01N 33/68* (2006.01)

(52) U.S. Cl.
CPC ........ *G01N 33/6881* (2013.01); *G01N 2333/78* (2013.01); *G01N 2800/40* (2013.01)

(58) Field of Classification Search
CPC .... G01N 2333/78; C07K 14/78; C07K 16/18; C07K 7/02
See application file for complete search history.

(56) References Cited

U.S. PATENT DOCUMENTS

| | | |
|---|---|---|
| 4,340,581 A | 7/1982 | Timpl |
| 4,946,778 A | 8/1990 | Ladner |
| 5,300,434 A | 4/1994 | Eyre |
| 5,316,914 A | 5/1994 | Oshima |
| 5,320,970 A | 6/1994 | Eyre |
| 5,342,756 A | 8/1994 | Risteli |
| 5,354,690 A | 10/1994 | Tryggvason |
| 5,532,169 A | 7/1996 | Eyre |
| 5,538,853 A | 7/1996 | Risteli |
| 5,641,837 A | 6/1997 | Eyre |
| 5,652,112 A | 7/1997 | Eyre |
| 5,656,439 A | 8/1997 | Eyre |
| 5,677,198 A | 10/1997 | Eyre |
| 5,701,902 A | 12/1997 | Vari |
| 5,741,652 A | 4/1998 | Shibuya |
| 5,753,450 A | 5/1998 | Baylink |
| 5,834,221 A | 11/1998 | Eyre |
| 5,834,610 A | 11/1998 | Johnson |
| 5,919,634 A | 7/1999 | Eyre |
| 5,939,274 A | 8/1999 | Eyre |
| 5,962,639 A | 10/1999 | Eyre |
| 5,965,136 A | 10/1999 | Baylink |
| 6,007,980 A | 12/1999 | Reeders |
| 6,010,862 A | 1/2000 | Eyre |
| 6,027,903 A | 2/2000 | Eyre |
| 6,048,705 A | 4/2000 | Eyre |
| 6,100,379 A | 8/2000 | Eyre |
| 6,143,511 A | 11/2000 | Eyre |
| 6,153,732 A | 11/2000 | Eyre |
| 6,204,367 B1 * | 3/2001 | Eyre .......................... 530/389.1 |
| 6,419,924 B1 | 7/2002 | Sarras, Jr. |
| 6,509,450 B2 | 1/2003 | Eyre |
| 6,689,746 B2 | 2/2004 | Hudson |
| 6,887,659 B2 | 5/2005 | Eyre |
| 6,916,604 B2 | 7/2005 | Eyre |
| 7,015,048 B2 | 3/2006 | Delmas |
| 7,449,171 B2 | 11/2008 | Hellerstein |
| 2005/0287535 A1 | 12/2005 | McGrath |

FOREIGN PATENT DOCUMENTS

| | | |
|---|---|---|
| JP | 6125976 | 5/1994 |
| JP | 2001349888 | 12/2001 |

OTHER PUBLICATIONS

Sassi et al. (Radiotherapy and Oncology, vol. 58, 2001, pp. 317-323).*
Gunwar, et al., Properties of the collagenous domain of the alpha 3(IV) chain, the Goodpasture antigen, of lens basement membrane collagen, Selective cleavage of alpha (IV) chains with retention of their triple helical structure and noncollagenous domain, Journal of Biological Chemistry, vol. 266, No. 21, Jul. 1991, pp. 14088-14094, The American Society of Biochemistry and Molecular Biology, Inc., USA.
Martin et al., Basement membrane proteins: molecular structure and function, Advances in Protein Chemistry, vol. 39, pp. 1-50, 1988.
Rupert Timpl, Structure and biological activity of basement membrane proteins, European Journal of Biochemistry, vol. 180, pp. 487-502.
Alexander, Caroline M. and Werb, Zena Extracellular matrix degradation. In: Hay, Elizabeth D. (ed.) Cell Biology of Extracellular Matrix. 2nd ed. 1991 New York, NY: Plenum Press pp. 255-275.
Amir, Avraham Dr. "Objective skin burn assessment kit" Mor Research Applications Ltd—Diagnostica/project inside and Israel Tech Transfer Organization, ITTN Feb. 17, 2009. Retrieved from the Internet: URL:www.mor-research.com/diagnostica.asp and www.ittn.org.il/pdtphp?tech_id=22505> retrieved on Sep. 16, 2009.
Bolarin, D. M. and Azinge, E. C. (2007) Biochemical markers, extracellular components in liver fibrosis and cirrhosis. Nig Q J Hosp Med 17(1):42-52.
Eyre, David R. et al., (2008) Advances in collagen cross-link analysis. Methods 45(1):65-74.
Fox, A. et al., (2008) Quantification of circulating cell-free plasma DNA and endothelial gene RNA in patients with burns and relation to acute thermal injury. Burns 34(6):809-816.

(Continued)

*Primary Examiner* — Lisa Cook
(74) *Attorney, Agent, or Firm* — The Law Office of Michael E. Kondoudis

(57) ABSTRACT

The present invention relates to methods and kits for evaluating the severity of a burn injury, which are based on the detection in a clinical fluid sample of skin metabolism products, such as collagen peptides which are released upon collagen degradation or synthesis.

4 Claims, 2 Drawing Sheets

(56) References Cited

OTHER PUBLICATIONS

Hanson, Dennis A. and Eyre, David R. (1996) Molecular site specificity of pyridinoline and pyrrole cross-links in type I collagen of human bone. J Biol Chem 271(43):26508-26516.

Kannisto, M. et al., (1998) Bone mineral status after pediatric spinal cord injury. Spinal Cord 36(9):641-646.

Kaufmann, J. et al., (2003) Hydroxypyridinium collagen crosslinks in serum, urine, synovial fluid and synovial tissue in patients with rheumatoid arthritis compared with osteoarthritis. Rheumatology (Oxford) 42(2):314-320.

Kohda, K. et al., (1991) Diagnostic value of measurement of serum type I procollagen carboxy terminal peptides in patients with scirrhous carcinoma of the stomach. Gut 32(6):624-629.

Lamparter, Steffen et al., (2002) Doxycycline and tissue repair in rats. J Lab Clin Med 139(5):295-302.

Miyahara, Michinori et al., (1982) Formation of collagen fibrils in vitro by cleavage of procollagen with procollagen proteinases. J Biol Chem 257(14):8442-8448.

Ogawa, Tadao et al., (1982) A novel fluor in insoluble collagen: a crosslinking moiety in collagen molecule. Biochem Biophys Res Commun 107(4):1252-1247.

Parfitt, A. M. et al., (1987) Procollagen type I carboxy-terminal extension peptide in serum as a marker of collagen biosynthesis in bone. Correlation with Iliac bone formation rates and comparison with total alkaline phosphatase. J Bone Miner Res 2(5):427-436.

Querejeta, Ramon et al., (2000) Serum carboxy-terminal propeptide of procollagen type I is a marker of myocardial fibrosis in hypertensive heart disease. Circulation 101(14):1729-1735.

Risteli, Juha et al., (1993) Radioimmunoassay for the pyridinoline cross-linked carboxy-terminal telopeptide of type I collagen: a new serum marker of bone collagen degradation. Clin Chem 39(4):635-640.

Sassi, Mirja-Liisa et al., (2001) Type I collagen turnover and cross-linking are increased in irradiated skin of breast cancer patients. Radiother Oncol 58(3):317-323.

ISR of PCT/IL2009/000598 mailed Sep. 30, 2009.

* cited by examiner

MONITORING SKIN METABOLISM PRODUCTS FOR EVALUATING BURN INJURY

This application is the U.S. national stage of PCT/IL/2009/000598 filed on Jun. 16, 2009, which is based on and claims the benefit of U.S. Provisional Patent Application No. 61/061,669 filed on Jun. 16, 2008, the content of each of which is expressly incorporated herein in its entirety by reference hereto.

SUBMISSION OF SEQUENCE LISTING

The present application is being filed along with a Sequence Listing in electronic format via EFS-Web. The Sequence Listing is provided as a text file entitled SequenceListing.txt. That text file is 29 Kb in size and was created Mar. 2, 2011. The information in the electronic format of the Sequence Listing is incorporated herein by reference in its entirety into this specification.

FIELD OF THE INVENTION

The present invention relates to methods and kits for evaluating the severity of a burn injury, which are based on the detection in a clinical fluid sample of skin metabolism products, such as collagen peptides which are released upon collagen degradation or synthesis.

BACKGROUND OF THE INVENTION

Skin is composed of a thin outer layer, the epidermis, and a thicker inner layer, the dermis, which are separated by the basement membrane. Subcutaneous tissue is located beneath the dermis, which contains mostly fat, and beneath that fasciae and muscles are found. The epidermis forms a tough, waterproof protective coating that contains dead cells on its outside surface and living cells on its inner side. The living cells replace the dead cells that are continually worn away. The dermis is a living tissue containing blood vessels, nerves, sweat glands and hair follicles.

Collagen is the main protein of connective tissue in animals, and its fibrillar form gives skin its mechanical strength. Each collagen fiber is composed of three long, helical polypeptide chains that bind tightly to each other. Synthesis and breakdown of collagen is indicative of skin integrity as well as of various skin diseases and disorders.

Collagen type I is synthesized as procollagen with a small amino terminal and a larger carboxy terminal propeptide, respectively termed procollagen type I amino terminal peptide (PINP) and type I procollagen carboxy terminal peptide (PICP). Once secreted into the extracellular space, the propeptides are removed by specific endopeptidases, thus allowing integration of the rigid collagen triple helix into the growing fibril (Miyahara et al. (1982) J Biol Chem. 257:8442-8448). The 100 kD PICP formed during this process is released into the blood. A stoichiometric ratio of 1:1 exists between the number of collagen molecules produced and that of PICP released.12 Therefore, the serum concentration of PICP has been proposed as a marker of collagen type I synthesis (Parfitt et al. (1987) J Bone Miner Res. 2:427-436).

Collagen type I carboxy terminal cross-linked telopeptide (abbreviated as CTX-I or CITP) is a 12 kD peptide produced, together with other peptides, when collagen fibrils undergo resorption (Alexander et al. Extracellular matrix degradation. In: Hay ed. Cell Biology of Extracellular Matrix. 2nd ed. New York, N.Y.: Plenum Press pp. 255-275). CITP is constituted by the carboxy terminal telopeptide (CTP) parts of two $\alpha_1$ chains of one collagen molecule and one $\alpha_1$ or $\alpha_2$-derived helical chain of another collagen molecule, cross-linked by a pyridinoline ring. This peptide is found in an immunochemically intact form in blood, where it appears to be derived from tissues (Risteli et al. (1993) Clin Chem. 39:635-640).

Osteoporosis, characterized by a decrease in bone mass, is associated with collagen degradation, specifically degradation of type I collagen which is the major organic component in the bone. Direct estimation of type I collagen degradation can be made by measuring the amount of type I collagen carboxy terminal telopeptide (C-telopeptide, CTP-I), or the amount of type I collagen amino terminal telopeptide (N-telopeptide, NTP-I), which are non-triple helical extension peptides found respectively at the C-terminal and the N-terminal ends of the collagen fiber.

For example, U.S. Pat. No. 5,538,853 discloses the use of antibody raised against type I collagen carboxy terminal cross-linked telopeptide isolated from decalcified human or animal bone for determining the concentration of liberated CTP in a sample, particularly serum or urine, to assess the degradation of type I collagen. Kits for bone degradation assays based on this disclosure are commercially available (Orion Diagnostica, Espoo, Finland).

U.S. Pat. No. 5,753,450 discloses assays for monitoring the levels of the C-telopeptide of human type I collagen as a marker for collagen degradation and specific indicator of bone resorption.

Pyridinoline and deoxypyridinoline collagen cross-link molecules also used as bone resorption markers. The relative levels of pyridinoline and deoxypyridinoline in urine from patients with rheumatoid arthritis has been disclosed as a marker of synovial tissue collagen degradation for that disease (Kaufmann J. et al. (2003) Rheumatology (Oxford) 42(2):314-20).

Serum levels of type I procollagen carboxy terminal propeptide (PICP) have been disclosed to be indicative of the clinical course of scirrhous carcinoma of the stomach (Kohda et al. (1991) Gut 32(6):624-629), and of myocardial fibrosis in hypertensive heart disease (Querejeta et al. (2000) Circulation 101:1729).

U.S. Pat. No. 6,916,604 discloses a method of assaying type I collagen fragments in a body fluid sample, comprising contacting the body fluid with a synthetic type I collagen N-telopeptide sequence, and an antibody immunoreactive with said sequence, using a competitive binding assay.

U.S. Pat. No. 6,509,450 discloses an immunoassay kit for the quantification of degradation products of carboxy-terminal telopeptides of type I collagen in a human serum sample.

U.S. Pat. No. 6,204,367 discloses an enzyme linked immunosorbent assay kit for the quantification of degradation products of carboxy-terminal telopeptides of type I collagen in a human serum sample.

U.S. Pat. No. 6,153,732 discloses a kit for detecting an analyte indicative of type II collagen resorption in vivo.

Basement membrane is a highly specialized part of the extracellular matrix that forms thin sheets that separate the cells of organs from the fibrillar connective tissues. The basement membrane is composed of several proteins, many of which are found only in these structures. Type IV collagen is the major structural component but other specific protein components include laminin, entactin (nidogen), perlecan, $\alpha 6$-$\beta 4$-integrin and proteoglycans. Additionally, the basement membrane may contain fibronectin and type VII collagen, that are also present in other extracellular matrices. It is currently believed that there are several proteins that are specifically found in basement membrane of certain tissues.

For example, the protein known as pemphigoid antigen appears to be limited to the basement membrane of skin.

An assay for detecting serum levels of collagen IV and laminin and use thereof for monitoring liver diseases has been disclosed (Bolarin et al (2007) Nig. Q. J. Hosp. 17(1):42-52).

Heating of the skin, however brief, can cause damage to the cells of its living tissue. Such damage typically is referred to as a burn. Generally, skin burns are categorized into degrees that indicate the depth of the burn injury. First degree burns cause redness of the skin and affect only the epidermis. Such burns heal quickly, but the damaged skin may peel away after a day or two. "Sunburn" is an example of a first degree burn. A second degree burn damages the skin more deeply, extending into the dermis and usually causes blistering. However, some of the dermis is left to recover. A third degree burn destroys the full thickness of the skin. In fourth degree burn, the burn extends beyond the skin to the fat, muscle and bone.

Experience has shown that second degree superficial dermal (or partial-thickness) burns will normally heal spontaneously within two weeks with minimal scarring, whereas deep dermal second degree and third degree (or full-thickness) burns usually result in necrotic skin and in very slow wound healing.

It is of major clinical importance to diagnose the depth of the burn as early as possible in order to determine the optimal course of patient treatment. However, it is usually almost impossible to assess the exact degree of the burn in the first 48-72 hours after the burn has been sustained.

Several methods have been proposed for evaluating burn injury, particularly to distinguish necrotic tissue from viable tissue. Clinical criteria utilized to distinguish burn depth include sensitivity to pin prick, visual appearance, and viable cutaneous circulation, but these criteria are not objective and they do not constitute a practical method for evaluating burn injury. Imaging techniques such as passive infrared thermography, laser Doppler, false-positive images, and high-frequency ultrasound are expensive and not sufficiently informative. Intravenous administration of fluorescent drugs such as indocyanine green and fluorescein, followed by detection with a fiber-optic instrument, has been attempted with limited success. Such techniques are hampered by the period of time required for the fluorescent drugs to reach the burn site and/or the time required for their clearance from the burn site, thus limiting the frequency of testing. Further, intravenous administration is counter-indicated in many burn cases since burn patients frequently suffer from vasoconstriction at the early stages.

The prior art does not teach or suggest that measurement of collagen or basement membrane degradation products may be used for the evaluation of burn severity.

There remains an unmet need for accurate, rapid and low cost methods and kits for evaluating the severity of a burn injury.

SUMMARY OF THE INVENTION

The present invention provides a rapid and cost-effective method and kit for accurate evaluation of the severity of a burn soon after it is sustained. The invention is based on measurement of the level of skin metabolism products in a clinical sample, particularly blood, using protein detection methods.

The present invention is based in part on the unexpected discovery that the presence and concentration of collagen and/or basement membrane degradation products in a blood sample taken from a subject suffering from a burn is indicative both of the percentage of body surface area affected by a deep burn, and of the depth of the burn wound, at the earliest stage of burn examination. The teachings of the present invention are exemplified by measuring collagen degradation products as markers of the severity of a burn of the dermis. However, it is to be understood that the methods of the present invention may be alternatively or additionally carried out by measurement of other skin metabolism products. Particularly, the methods of the present invention include measuring collagen synthesis products, including but not limited to, type I procollagen carboxy terminal peptide (PICP) and type I procollagen amino terminal peptide (PINP), as well as degradation products of protein components of the basement membrane, including but not limited to, type IV collagen, type VII collagen, laminin, entactin (nidogen), perlecan, $\alpha 6$-$\beta 4$-integrin, fibronectin and proteoglycans. According to the invention the levels of these peptides are indicative markers for burns of severity greater than first degree.

Thus, according to one aspect, the present invention provides a method for evaluating the severity of a burn injury in a subject in need thereof, the method comprising:

obtaining a biological fluid sample from the subject; and detecting the level in the sample of at least one proteinaceous skin metabolism product;

wherein the level of the at least one skin metabolism product in said sample is indicative of the severity of the burn.

In accordance with the invention, the term "severity of the burn" refers to one or more of the parameters of: the degree of burn, the percentage of the total body surface area affected by the burn and the depth of the burn.

According to certain embodiments, the biological fluid sample is selected from the group consisting of blood, plasma, serum and urine.

According to certain embodiments, the skin metabolism product is selected from the group consisting of a collagen degradation product, a collagen synthesis product and a basement membrane degradation product. According to certain embodiments, the collagen degradation product is selected from the group consisting of carboxy terminal telopeptide of type I collagen (CTP-I); amino terminal telopeptide of type I collagen (NTP-I); cross-linked carboxy terminal telopeptide of type I collagen (CTX-I); cross-linked amino terminal telopeptide of type I collagen (NTX-I); pyridinoline (Pyr), and deoxypyridinoline (D-Pyr). According to certain embodiments, the collagen synthesis product is selected from the group consisting of type I procollagen carboxy terminal peptide (PICP) and type I procollagen amino terminal peptide (PINP).

In particular embodiments, the carboxy terminal telopeptide of type I collagen is selected from the group consisting of SEQ ID NO:1; SEQ ID NO:4; SEQ ID NO:5 and SEQ ID NO:6. In particular embodiments, the cross-linked carboxy terminal telopeptide of type I collagen comprises at least one of SEQ ID NO:1; SEQ ID NO:2; SEQ ID NO:3; SEQ ID NO:20; SEQ ID NO:21; SEQ ID NO:22 and SEQ ID NO:23. In particular embodiments, the cross-linked carboxy terminal telopeptide of type I collagen comprises SEQ ID NO:1 and one of SEQ ID NO:2 or SEQ ID NO:3. In particular embodiments, the amino terminal telopeptide of type I collagen is selected from the group consisting of SEQ ID NO:7; SEQ ID NO:8, and SEQ ID NO:9. In particular embodiments, the cross-linked amino terminal telopeptide of type I collagen comprises SEQ ID NO:8 and SEQ ID NO:19. In particular embodiments, the type I procollagen carboxy terminal peptide comprises SEQ ID NO:15. In particular embodiments, the type I procollagen amino terminal peptide comprises SEQ ID NO:16. According to particular embodiments, the collagen degradation product is C-telopeptide, particularly CTP of type I collagen, or fragments thereof.

According to other embodiments, the basement-membrane degradation product is selected from the group consisting of collagen type IV, collagen type VII, laminin, entactin, perlecan, α6-β4-integrin, fibronectin and fragments thereof.

In particular embodiments, the collagen type IV is selected from the group consisting of SEQ ID NO:24; SEQ ID NO:25; SEQ ID NO:26; SEQ ID NO:27; SEQ ID NO:28; SEQ ID NO:29 and SEQ ID NO:30.

According to particular embodiments, the step of detecting comprises use of an antibody reagent that is specific for the skin metabolism product. According to particular embodiments, the step of detecting comprises an immunoassay. In particular embodiments, the immunoassay comprises at least one of a radioimmunoassay (RIA), an enzyme-linked immunosorbent assay (ELISA), an immunofluorescence assay (IFA), a membrane-based lateral flow immunochromatographic assay, a solid phase chromatography assay and an antibody microarray. In particular embodiments, the immunoassay comprises a plurality of antibody reagents for detecting a plurality of skin degradation products. According to particular embodiments, the antibody is selected from a polyclonal antibody and a monoclonal antibody.

According to certain embodiments, the method further comprises correlating the level of the skin degradation product detected in the sample with at least one reference level, so as to determine at least one parameter selected from the group consisting of the percentage of body surface area affected with a particular degree of burn, and the depth of a burn. For example, the level of a skin metabolism product, or a set of skin metabolism products in the sample may be indicative of a first, second, third or forth degree burn, or the relative percentage of body surface area affected by a burn.

In particular embodiments, the method comprises correlating the level of at least one collagen degradation product detected in the sample with at least one reference level, so as to determine the depth of the burn. In particular embodiments, the method comprises correlating the level of at least one basement membrane degradation product detected in the sample with at least one reference level, so as to determine the percentage of the total body surface area affected by the burn. In a particular embodiment, the basement membrane degradation product is a type IV collagen.

In particular embodiments, the method is carried out within 24 hours from occurrence of the burn injury in the subject. In particular embodiments, the method is carried out within 4 hours from occurrence of the burn injury in the subject. In particular embodiments, the method is carried out within 2 hours from occurrence of the burn injury. In particular embodiments, the method is carried out at periodic intervals following burn injury so as to monitor the progress of wound healing at the burn site. In particular embodiments, the intervals are of 24 to 168 hours. In particular embodiments, the intervals are daily intervals. In particular embodiments, the intervals are weekly intervals.

The methods of the present invention are useful for evaluating burn injury regardless of the burn cause. According to certain embodiments, the burn is the result of an external aggravation selected from the group consisting of heat, cold, electricity flow through a subject body and exposure to chemical agents, including acids and high alkaline materials.

The method of the present invention is of use for evaluating burn degree in humans and non-human mammals. In non-human mammals similar assessments may be made which may have use in veterinary or in the assessment of pharmaceuticals for treating burns.

In another aspect, the invention provides a kit for determining the severity of a burn, the kit comprising at least one antibody reagent suitable for detecting the level of at least one skin metabolism product in a biological fluid sample from a subject, and instructional material for using the kit to determine the severity of a burn in the subject, by correlating the detected level of the at least one skin metabolism product in the sample, with a reference level corresponding to a particular degree of burn severity. In particular embodiments, the kit comprises a plurality of antibody reagents. In particular embodiments, the instructional material is further for using the kit to determine the percentage of body surface area in the subject affected with a particular degree of burn.

Other objects, features and advantages of the present invention will become clear from the following description.

DETAILED DESCRIPTION OF THE INVENTION

Figure 1:
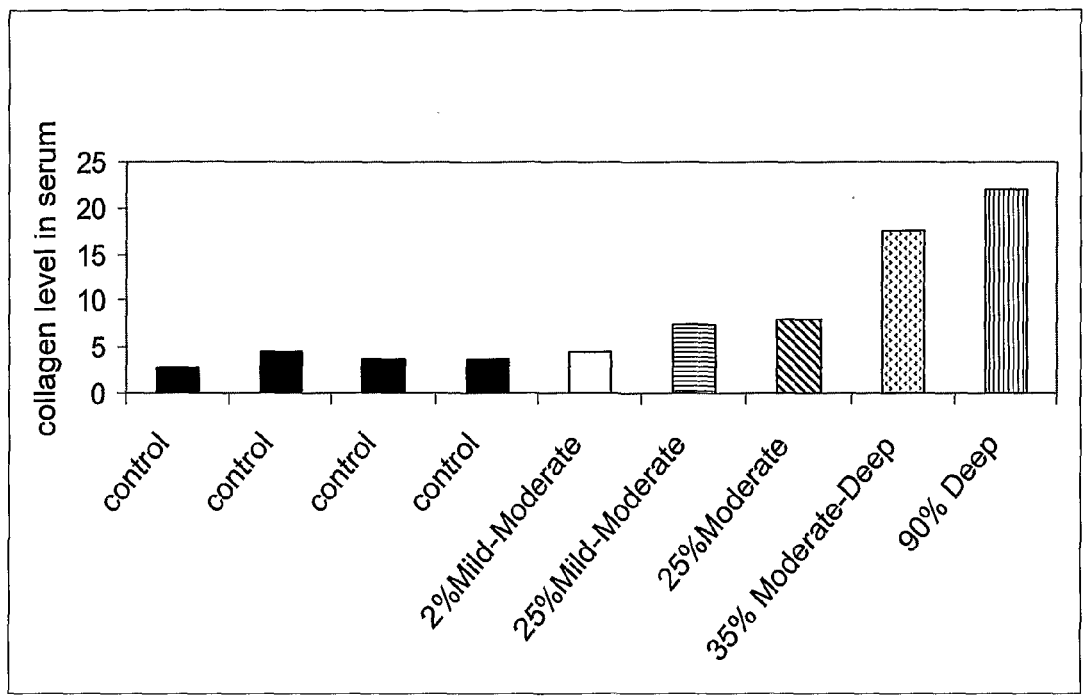
FIG. 1 shows the correlation between CTP level detected in patient blood samples collected within 3 hours of burn injury, and burn severity.

The present invention provides a method for burn evaluation that allows a physician or emergency medical service (EMS) personnel to make a quick and accurate evaluation of the extent and depth of a burn injury to the skin at the earliest stage of patient examination. The method may be carried out at on-site at the location at which the burn injury was sustained, in an emergency medical setting or at a fully equipped medical facility. The present invention discloses for the first time that monitoring the presence and level of skin degradation and synthesis products, particularly of C-telopeptide, is be indicative of the extent of damage caused to the skin as well as to adjacent collagen-containing tissues due to a burn.

DEFINITIONS

As used herein, the term "burn" refers to an injury to tissues caused by heat, cold, chemicals, electricity, or irradiation effects.

As used herein, the term "severity of the burn" refers to one or more parameters used to classify a burn, such as the degree of burn, the percentage of the total body surface area affected by the burn and the depth of the burn.

The most common type of burn is that which results from thermal injury, in which some portion of the body surface is exposed to either moist or dry heat of sufficient temperature to cause local and systemic reactions. Clinically, the extent of such a burn is often expressed as first degree, second degree, and so forth. Different systems of classification of burn degrees are known in the art.

First degree burns result in some redness and swelling of the injured part, without necrosis of any tissue or the formation of blisters. Healing is completed in a few days without scarring, as the damage is at the epidermis only.

Second degree burns show a variable destruction of parts of the dermis so that blistering occurs. Healing by regeneration in such superficial burns does not necessitate skin grafting, unless secondary infections ensue. Typically, no scarring results from second degree burns.

Third degree burns are marked by complete destruction of a skin region, including the necrosis of accessory skin structures such as hair and sweat glands. A brownish-black eschar (a dry scab or slough) marks the destroyed tissue. This is sloughed off and that defect becomes filled with granulation tissue that later consolidates and changes to form a dense, thick scar. Complications may occur without adequate care, and grafting is not unusual, sometimes being required because of contracture of the scar tissue. In deep third degree burns, also classified as fourth degree burns, tissue is destroyed to the level of or below the deep fascia lying beneath the subcutaneous fat and connective tissue of the body. Muscle, bone, deeper nerves, and even organs may be injured or destroyed by this severe degree of burn. Healing is usually a slow, involved process, requiring much reparative and reconstructive work by surgical specialists.

Electrical burns result from the amount of heat incident to the flow of a certain amount of electricity through the resistance offered by tissues. From a practical standpoint, most of the resistance offered to the passage of an electric current is that of the skin and the interface between the skin and the external conductor. Therefore, most electrothermal injuries are limited to the skin and immediately subjacent tissues, although deep penetration may follow large voltages.

Most chemical burns result from the action of corrosive agents which destroy tissues at the point of contact. Exposure of the skin, eyes, and gastrointestinal tract are common.

The term "metabolism product" as used herein refers to any molecule produced from the biochemical conversion of one molecule into a related molecule by a reaction or series of reactions. A metabolism product includes both catabolic and anabolic products as defined herein.

As used herein the term "skin metabolism product" refers to any proteinaceous product deriving from skin degradation or synthesis.

The terms "degradation product" and "catabolic product" are used herein interchangeably to refer to any compound that is produced as a result of catabolism. Catabolism generally refers to a process in which a molecule is broken into smaller parts. The term "skin degradation product" thus refers to a proteinaceous molecule derived from a catabolic process of a component of skin. The opposite of catabolism is anabolism in which molecules are synthesized from smaller subunits. The term "skin synthesis product" thus refers to a proteinaceous molecule formed in an anabolic process for formation of a component of skin.

The terms "collagen carboxy terminal peptide", "C-telopeptide" and "CTP" are used herein interchangeably, referring to sequences of about 12 to 29 amino acids that occur at C-terminus of the tropocollagen molecule, particularly of type I collagen but also of other collagen types, including type II collagen, type III collagen and type IV collagen. The terms refer to a class of species, the class including a mixture of peptide species, among them crosslinked species as well as non-crosslinked. The teaching of the present invention explicitly includes the detection of peptides which are immunoreactive fragments of CTP, using adequate antibodies.

The terms "collagen amino terminal peptide", "N-telopeptide" and "NTP" are used herein interchangeably, referring to sequences of about 12 to 29 amino acids that occur at N-terminus of the tropocollagen molecule, particularly of type I collagen but also of other collagen types, including type II collagen, type III collagen and type IV collagen. The terms refer to a class of species, the class including a mixture of peptide species, among them crosslinked species as well as non-crosslinked. The teaching of the present invention explicitly includes the detection of peptides which are immunoreactive fragments of NTP, using adequate antibodies.

As used herein, the term "tropocollagen" refers to the molecular component of a collagen fiber, consisting of three polypeptide chains coiled around each other.

The term "antibody" (or "antibodies") is used herein in the broadest sense and refers to intact molecules as well as fragments thereof, which binds specifically to an antigenic determinant, and specifically, binds to proteins or peptides identical or structurally related to the antigenic determinant which stimulated their production. Thus, antibodies are useful in assays to detect the antigen which stimulated their production.

"Antibody fragments" comprise a portion of a full-length antibody, generally the antigen binding or variable region thereof. Examples of antibody fragments include Fab, Fab', F(ab')2, and Fv fragments; diabodies; linear antibodies; single-chain antibody molecules; and multi-specific antibodies formed from antibody fragments. According to certain embodiments of the present invention, the presence or level of collagen or basement-membrane degradation products in a blood sample taken for the evaluation of burn injury is monitored by antibodies which specifically bind to CTP or fragments thereof. According to certain embodiments, the antibodies specifically bind to an antigen selected from the group consisting of collagen type I, CTP, collagen IV, laminin and fragments thereof.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries, as is known in the art, for example using techniques such as those described in Clackson et al., Nature 352:624-628 (1991) and Marks et al., J. Mol. Biol. 222:581-597 (1991).

In some embodiments, monoclonal and polyclonal antibodies are used as crude preparations, while in preferred embodiments, these antibodies are purified. For example, in some embodiments, polyclonal antibodies contained in crude antiserum are used. Also, it is intended that the term "antibody" encompass any immunoglobulin (e.g., IgG, IgM, IgA, IgE, IgD, etc.) obtained from any source (e.g., humans, rodents, non-human primates, lagomorphs, caprines, bovines, equines, ovines, etc.).

As used herein, the terms "antigen" and "immunogen" are used in reference to any substance that is capable of being recognized by an antibody, and which is capable of inducing the formation of antibodies, either on its own or in combination with a hapten or adjuvant. Thus, in an immunogenic reaction, antibodies are produced in response to the presence of an antigen or portion of an antigen.

It is intended that the terms antigen and immunogen encompass protein molecules or portions of protein molecules, which contains one or more epitopes. The term "epitope" as used herein, refers to that fragment of a molecule that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as "epitopes" or "antigenic determinants". An antigenic determinant may compete with the intact antigen (i.e., the immunogen used to elicit the immune response) for binding to an antibody. The teaching of the present invention makes use of the capability of collagen C-telopeptide, collagen type IV, laminin or fragment thereof to function as antigens which form an antigen-antibody complex upon contacting a sample containing such antigens with an appropriate antibody.

As used herein, the terms "antigen fragment" and "portion of an antigen" and the like refer to a portion of an antigen. Antigen fragments or portions typically range in size, from a small percentage of the entire antigen to a large percentage, but not 100%, of the antigen. In some embodiments, antigen fragments and/or portions therefrom, comprise an "epitope" recognized by an antibody, and are therefore referred to as "immunoreactive fragments".

The terms "specifically interacts" and "specifically binds" are used herein interchangeably to refer to high avidity and/or high affinity binding of a reagent, such as an antibody to a specific peptide or epitope thereof, e.g., a CTP or NTP peptide. Antibody binding to its epitope is stronger than binding of the same antibody to any other epitope, particularly those which may be present in molecules in association with, or in the same sample, as the specific polypeptide of interest. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g., by use of appropriate controls.

The term "primary antibody" as used herein refers to an antibody which binds specifically to the target protein antigen in a biological or test sample. A primary antibody is generally the first antibody used in an immunoassay procedure. In some embodiments, the primary antibody is the only antibody used in an immunoassay procedure.

The term "secondary antibody" as used herein refers to an antibody which binds specifically to a primary antibody, thereby forming a bridge between the primary antibody and a subsequent reagent, if any. The secondary antibody is typically directed against the Fc portion of the immunoglobulin type of the primary antibody (e.g., anti-mouse Fc antibody).

The terms "label", "reporter reagent", "reporter molecule", "detectable label", "detection substrate" and "detection reagent" are used herein interchangeably in reference to a reagent which is conjugated or fused directly or indirectly to a reagent such as an antibody which permits the detection and/or quantitation of an antibody bound to an antigen. The label may itself be detectable (e.g., radioisotope labels or fluorescent labels) or, in the case of an enzymatic label, may catalyze chemical alteration of a substrate compound or composition which is detectable.

Description of Particular Embodiments

The present invention provides a method for immediate and accurate evaluation of the severity of a burn injury in a subject, the method comprising:

providing a biological fluid sample from the subject; and
detecting the level in the sample of at least one proteinaceous skin metabolism product;
wherein the level of the at least one skin metabolism product in said sample is indicative of the severity of the burn.

According to certain embodiments, the biological fluid sample may be any of blood, plasma, serum, urine or saliva.

The skin metabolism product may be any of a collagen degradation product, a collagen synthesis product or a basement membrane degradation product. In particular embodiments, the collagen degradation product may be any of carboxy terminal telopeptide of type I collagen (CTP-I); amino terminal telopeptide of type I collagen (NTP-I); cross-linked carboxy terminal telopeptide of type I collagen (CTX-I); cross-linked amino terminal telopeptide of type I collagen (NTX-I); pyridinoline (Pyr), or deoxypyridinoline (D-Pyr). In a particular embodiment, the skin metabolism product is a carboxy terminal telopeptide of type I collagen.

In particular embodiments, the carboxy terminal telopeptide of type I collagen is selected from the group consisting of SEQ ID NO:1; SEQ ID NO:4; SEQ ID NO:5 and SEQ ID NO:6. In particular embodiments, the cross-linked carboxy terminal telopeptide of type I collagen comprises at least one of SEQ ID NO:1; SEQ ID NO:2; SEQ ID NO:3; SEQ ID NO:20; SEQ ID NO:21; SEQ ID NO:22 and SEQ ID NO:23. In particular embodiments, the cross-linked carboxy terminal telopeptide of type I collagen comprises SEQ ID NO:1 and one of SEQ ID NO:2 or SEQ ID NO:3, as disclosed for example in U.S. Pat. No. 5,538,853. In particular embodiments, the cross-linked carboxy terminal telopeptide of type I collagen comprises SEQ ID NO:20; SEQ ID NO:21; SEQ ID NO:22 and SEQ ID NO:23, as disclosed for example in U.S. Pat. No. 5,300,434. In particular embodiments, the amino terminal telopeptide of type I collagen is selected from the group consisting of SEQ ID NO:7; SEQ ID NO:8, and SEQ ID NO:9. In particular embodiments, the cross-linked amino terminal telopeptide of type I collagen comprises SEQ ID NO:8 and SEQ ID NO:19, as disclosed for example in U.S. Pat. No. 5,300,434.

In particular embodiments, the type I procollagen carboxy terminal peptide comprises SEQ ID NO:15. In particular embodiments, the type I procollagen amino terminal peptide comprises SEQ ID NO:16.

Various cross-linked carboxy terminal and amino terminal telopeptides of type I, type II and type III collagen, are disclosed for example in U.S. Pat. No. 5,300,434.

Various type I, type II and type III human collagen degradation products and methods to detect same in clinical samples are disclosed, for example in U.S. Pat. Nos. 6,916,604; 6,509,450; 6,204,367; 6,153,732; 6,143,511; 6,100,379; 6,048,705; 6,027,903; 6,010,862; 5,962,639; 5,939,274; 5,919,634; 5,834,221; 5,677,198; 5,656,439; 5,652,112; 5,641,837; and 5,320,970.

In other embodiments, the skin metabolism product is a collagen synthesis product such as type I procollagen carboxy terminal peptide (PICP) or type I procollagen amino terminal peptide (PINP). For example, the procollagen I carboxy terminal peptide may comprise SEQ ID NO:16, or the procollagen type I amino terminal peptide may comprise SEQ ID NO:17.

According to other embodiments, the basement-membrane degradation product is selected from the group consisting of collagen type IV, collagen type VII, laminin, entactin, perlecan, α6-β4-integrin, fibronectin and fragments thereof.

In particular embodiments, the collagen type IV is selected from the group consisting of SEQ ID NO:24; SEQ ID NO:25; SEQ ID NO:26; SEQ ID NO:27; SEQ ID NO:28; SEQ ID NO:29 and SEQ ID NO:30.

In particular embodiments, the method comprises correlating the level of at least one collagen degradation product detected in the sample with at least one reference level, so as to determine the depth of the burn. In particular embodiments, the method comprises correlating the level of at least one basement membrane degradation product detected in the sample with at least one reference level, so as to determine the percentage of the total body surface area affected by the burn. In a particular embodiment, the basement membrane degradation product is a type IV collagen.

The present invention is based on the observation that serum levels of CTP-I are indicative of the severity of a burn injury, including the relative percentage of body surface area affected with a burn and the depth of a burn. As disclosed in Example 2 and FIG. 1 herein, burn patients with increasingly severe degrees of burn injuries have correspondingly greater serum levels of CTP-1. Since increased serum levels of CTP-1 are apparent in blood soon after burn injury is sustained, the present invention provides a reliable and objective means of assessing burn injury, both upon initial intake, and during the course of treatment. As disclosed in Example 3 and FIG. 2, in at least some patients, CTP-1 levels decrease as the healing process progresses.

In a typical case of burn injury, a patient sustains a burn in a fire. A large part of the body will likely be affected, for example the entire upper part of the body will be red and blistering. Even upon admission to a medical facility, it is frequently impossible to determine if the patient should be transferred to a burn center. It is further difficult to evaluate the extent of the deep burn and hence to calculate the amount of i.v. fluids that should be given. Additional management decisions which require a clear picture of the burn severity include the optimal nutrition plan, and the amount of skin required for skin grafting. Further, the prognosis depends on the burn severity. Measuring skin degradation products as described herein above and demonstrated for several individuals (see FIG. 2) provides a clear guideline as to the severity of the burn and the body surface area involved so that rational management decisions may be taken.

The method is preferably carried out within about 24 hours from the time when the subject sustained the burn injury, more preferably, within about 4 hours and most preferably within about 2 hours.

Further, the method may be carried out at periodic intervals following burn injury so as to monitor the progress of wound healing at the burn site. For example, the intervals may be spaced by about 24 to about 168 hours. In particular embodiments, the intervals are daily intervals. In particular embodiments, the intervals are weekly intervals. In clinical practice, it may be desirable to initially monitor the patient daily, for example in the first seven days following injury, and thereafter every two days, or in accordance with any schedule deemed appropriate by a medical practitioner of skill in the art.

According to certain embodiments, the method further comprises correlating the level of the skin degradation product detected in the sample with at least one reference level, so as to determine the percentage of body surface area affected with a particular degree of burn. That is, the level of a skin metabolism product, or a set of skin metabolism products in the sample is indicative of first, second, third or forth degree burn, and reflects the relative percentage of body surface area affected by each burn degree.

Collagen

Collagen is the major fibrous protein in animals, present in all types of multicellular animals and probably the most abundant animal protein in nature. It is estimated that collagen accounts for about 30% of the total human body protein. Collagen is located in the extracellular matrix of connective tissues. It is part of the interacting network of proteoglycans and proteins that provides a structural framework for both soft and calcified connective tissues. By self-associating into fibrils and by binding to proteoglycans and other matrix components, collagen contributes to tissue integrity and mechanical properties. Collagen interacts with cells through the integrin cell receptors and mediates cellular adhesion and migration. Important roles for collagen have been identified in development, wound healing, platelet aggregation, and aging.

The classification of an extracellular matrix protein as a collagen is based on the presence of a domain with a distinctive triple-helical conformation. The collagen triple helix consists of three polypeptide chains supercoiled about a common axis and linked by hydrogen bonds. At least 19 distinct molecules have been classified as collagens, and specific types are associated with particular tissues. The most prevalent and well-studied collagens belong to the fibril-forming or interstitial collagen family. The molecules in a fibril are covalently cross-linked by an enzymatic mechanism to strengthen and stabilize them. Inhibition of the enzyme involved in cross-linking results in a dramatic decrease in the tensile strength of tissues, a condition known as lathyrism.

Type I is the most common fibril-forming collagen. Its fibrils make up the mineralized matrix in bone, the strong parallel bundles of fibers in tendon, and the plywood like alternating layers in the transparent cornea. Type II is the major fibril-forming collagen in cartilage, while type III is found in blood vessels and skin, together with type I. Basement membranes, which serve to separate cell layers and act as filtration barriers, contain a distinctive group of collagens, denoted as type IV collagens, which are organized into a network or meshlike sheet structure.

An orderly breakdown of collagen is necessary during development and tissue remodeling. An abnormal increase in the degradation of cartilage collagen is seen in osteoarthritis. Collagen breakdown also appears to be essential for tumor metastases. A number of hereditary diseases have been shown to be due to mutations in specific collagen genes. Osteogenesis imperfecta (brittle bone) disease is characterized by fragile bones and is due to mutations in type I collagen. Some cartilage disorders are caused by mutations in type II collagen. Ruptured arteries are found in Ehlers-Danlos syndrome type IV, which arises from mutations in type III collagen. C-telopeptide is a non-triple helical peptide of about 24 amino acids located at the C-terminal end of the collagen fiber. The concentration of this peptide in collagen is uniform, and thus it is highly suitable as a measure of collagen degradation. Indeed, CTP and immunoreactive fragments thereof have been suggested for the determination of collagen degradation and bone resorption (see, for example, U.S. Pat. Nos. 5,532,169; 5,538,853; 5,753,450; and 5,965,136) and various kits, particularly kits based on the detection of C-telopeptide of the a(I) claim of collagen type I, are currently in use. Exemplary methods for isolating type I collagen carbody terminal and amino terminal telopeptides, and methods of producing antibodies specifically binding them, are disclosed for example in U.S. Pat. Nos. 5,300,434 and 5,538,853.

Types I, II and III of collagen each have four lysine-mediated intermolecular cross-linking sites at equivalent locations in their molecules, one in each telopeptide and two others at sites in the tripe-helical domains. Both N-telopeptide-to-helix and C-telopeptide-to-helix cross-links occur, and upon maturation of connective tissues, stable non-reducible compounds are formed. The most widely distributed mature cross-links are the fluorescent compound hydroxylysylpyridinoline and its deoxy analog lysylpridinoline, also referred to respectively as pyridinoline (Pyr) and deoypyridinoline (D-Pyr) (see for example, Ogawa et al (1982) Biochem Biophys Res Commun 107:1252-1247; Hanson et al (1996) J Biol Chem 271(43):26508-16).

Basement membranes are complex, extracellular matrices that play a role in vital functions, such as embryogenesis, tissue organization, vascular architecture and kidney glomerular filtration. Basement membranes are found at the base of epithelial and endothelial cells and at the interface between cells and the connective tissue matrices. They are synthesized by a variety of cells including the endothelium of the capillaries, the epithelium of the kidney glomerulus and tubule, the parietal endoderm of the yolk sac, the epithelial cells of lens capsule, and the epithelium of glandular, respiratory and gastrointestinal tissues. The membranes undergo morphological and presumably functional changes under a variety of pathological states such as systemic lupus erythematosus, diabetes mellitus, Goodpasture's syndrome, and post-streptococcal glomerulonephritis. In these diseases, different tissues are affected e.g. in diabetes mellitus the basement membranes of both the kidney glomerulus and the capillaries of muscle are affected. The variety of functions of basement membranes suggests the possibility of microheterogeneity of the macromolecular components and diversity in their organization. Among the functions which have been ascribed to basement membranes are (a) filtration, notably of plasma in the kidney glomeruli, (b) organization of tissues and organs by delineation of boundaries between groups of cells and (c) provision of a matrix for cell adhesion.

The basement membranes are composed of several proteins, many of which are found only in these structures. Type IV collagen is the major structural component but other specific protein components include laminin, entactin (nidogen) and proteoglycans, including heparan sulphate and glycosaminoglycans. Additionally, the basement membranes may contain fibronectin and type VII collagen that are also present in other extracellular matrices.

As is true for collagens in general, type IV collagen molecules contain three α-chains that are coiled around each other to form a long triple-helical molecule that is about 1.5 nm in diameter and about 400 nm in length. The type IV collagen heterotrimer is characterized by three distinct structural domains: the non-collagenous (NCI) domain at the carboxyl terminus; the triple helical collagenous domain in the middle region; and the 7S collagenous domain at the amino terminus (Martin, et. al. (1988) Adv. Protein Chem. 39:1-50; Gunwar et al. (1991) J. Biol. Chem. 266:14088-14094). Single type IV collagen molecules are linked with each other into a complex, flexible network-like structure into which the other basement membrane components are bound (Timpl (1989) Eur. J. Biochem. 180:487-502). Six genetically distinct α-chains belonging to two classes with extensive homology have been identified, and their relative abundance has been demonstrated to be tissue specific.

Antibodies against human type IV collagen and methods of detecting type IV collagen in body fluids have been disclosed for example in U.S. Pat. Nos. 6,419,924; 5,741,652; 5,354, 690; 5,316,914; and 4,340581.

The term "laminin" includes a well defined family of glycoproteins that provide an integral part of the structural and functional scaffolding of almost every mammalian tissue, including basement membranes. The laminin is an adhesive glycoprotein-ligand composed of three sub-units with a molecular weight of 900,000 Daltons. Laminins possess the RGDS (Arg-Gly-Asp-Ser) sequence recognized by the transmembranal structure of the most common integrin ($\alpha 5\beta 1$). Laminin-integrin is known as a major cell-matrix binding structure. Each laminin is a heterotrimer assembled from alpha, beta and gamma chain subunits, secreted and incorporated into cell-associated extra-cellular matrices. There are five forms of alpha-chains: LAMA1, LAMA2, LAMA3, LAMA4, LAMA5; four form of beta-chains: LAMB1, LAMB2, LAMB3 and LAMB4 are known; and there are three types of gamma-chains: LAMC1, LAMC2, LAMC3. The different types of laminin (currently there are 15 known types) can self-assemble, bind to other matrix macromolecules, and/or interact with cells via integrin receptors, dystroglycon or any other even non-integrin receptors.

Assays for collagen type IV and laminin are known in the art, and available kits can be readily used. However, nowhere in the background art is it taught or suggested to employ measurements of the presence or level of CTP, NTP, collagen type IV or laminin as well other skin degradation products in a blood sample taken from a patient having a burn as a means for determining the severity of the burn. Determining the severity of a burn as fast as possible is highly important in the selection of treatment, which, by itself, has a significant impact on the burn healing process in terms of time, pain and hospitalization expenses. In addition, the level of such skin degradation products in the easy to obtain blood sample, can reflect the effectiveness of the treatments selected. For example, one of the major complications in case of a deep burn is that the burn is easily infected, and the infection worsens the burn degree. According to the teaching of the present invention, such worsening, or, to the contrary, improvement resulting from a certain treatment employed can be monitored quickly and accurately.

By way of illustration, the teachings of the present invention are exemplified by monitoring the presence and/or level of the collagen degradation product CTP. However, equivalent considerations and assays as are known to a person skilled in the art can be employed for evaluating the severity of a burn by monitoring the presence of the collagen degradation product NTP and/or level of other skin degradation products, particularly degradation products of the skin basement membrane as described hereinabove and as is known in the art.

According to certain embodiments, the C-telopeptide measured in accordance with the teaching of the present invention is C-telopeptide of type I collagen. The C-telopeptide can be either crosslinked or not crosslinked. However, it is likely that a blood sample taken from a patient having a burn will contain crosslinked CTP, as this form is resistant against further degradation.

Immunoassays

Immunoassays for detecting antigens of interest present in clinical fluid samples are known in the art and may be readily used for detecting skin metabolism products, such as CTP-I or NTP-I according to the present invention. Typically, the sample is a blood, serum, or urine sample. Suitable immunoassays include for example, radioimmunoassay, (RIA), fluorescent immunoassays, (FIA), enzyme-linked immunosorbant assays (ELISA), "sandwich" immunoassays, flow-through immunoassays, solid-phase chromatography immunoassays, gel diffusion precipitation reactions, immunodiffusion assays, precipitation reactions, agglutination assays, Western blots, immunoelectrophoresis assays (see for example, Harlow and Lane, Using Antibodies, A Laboratory Manual, Cold Spring Harbor Laboratory, New York (1999)). Furthermore, many different formats of the aforementioned assays are known in the art, any of which will find use in the present invention. Moreover, it is not intended that the present invention be limited to any of the aforementioned types of assays.

A suitable immunoassay for carrying out the invention typically employs an antibody reagent which specifically binds the target antigen of interest i.e. a skin metabolism product such as CTP-I. A biological fluid sample to be tested is brought into contact with the antibody and if target antigen is present in the sample, they will immunologically react to form antibody-antigen complexes which may then be detected and quantitatively measured. The antibody is generally and preferably in semi-purified or purified form so as to avoid non-specific interactions caused by contaminants such as interfering proteins. Detection of antibody-antigen complexes may be carried out either directly or indirectly.

In a direct assay, the binding of antibody to the target antigen is determined directly using a labeled reagent, such as a fluorescent labeled or an enzyme-labeled primary antibody, which can be detected without further antibody interaction. In a typical indirect assay, unconjugated primary antibody binds to the antigen and then a labeled secondary antibody (also termed "detection antibody") binds to the primary antibody. Signal amplification occurs because several secondary antibodies may react with different epitopes on the primary antibody. Alternately, both the primary and secondary antibodies may be unlabeled and labeled tertiary antibody is employed. Where the antibody (primary, secondary or tertiary) is conjugated to an enzymatic label, a chromagenic or fluorogenic substrate is added to provide detection of the antigen.

An indirect immunoassay may further incorporate an antigen-antibody competition assay, as further described below. In such assays, a purified antigen such as CTP-I may be used to determine if CTP-I is present in the sample by competing for the binding with an anti-CTP-I antibody.

The primary antibody (also termed "capture antibody") used for detection of the peptide or protein of interest is stably associated with e.g., directly or indirectly bound to, the surface of a solid support, e.g. column, microtiter plate, beads, membrane, typically made of glass, plastic, polysaccharides, nylon or nitrocellulose. A plurality of antibody reagents for detecting a plurality of skin metabolism products may be simultaneously bound to the same support, such as in an array.

The test sample is allowed to contact the support during a period of incubation, generally following blocking of non-specific binding sites with non-interfering proteins such as bovine serum albumin. After incubation with each reagent e.g. blocking agent, primary antibody, secondary antibody, the support is washed to remove non-bound components. Determination of suitable reagents, conditions for washing, incubation etc. is within the ability of one of average skill in the art.

Detectable labels suitable for conjugation to antibodies, antigens and other binding reagents include radioisotopes, fluorescent labels, enzyme-substrate labels, chromogenic labels, chemiluminescent labels and colloidal gold particles.

Radioisotopes include for example, $^{35}S$, $^{14}C$, $^{125}I$, $^3H$, $^{32}P$ and $^{131}I$. Fluorescent labels include for example, fluorescent molecules fluorescein isothiocyanate (FITC), rhodamine, phycoerythrin (PE), phycocyanin, allophycocyanin, orthophthaldehyde, fluorescamine, peridinin-chlorophyll a (PerCP), Cy3 (indocarbocyanine), Cy5 (indodicarbocyanine), lanthanide phosphors, and the like.

Enzymatic labels include luciferases (e.g. firefly luciferase and bacterial luciferase), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, for example: horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); alkaline phosphatase (AP) with para-nitrophenyl phosphate as chromogenic substrate; and β-D-galactosidase β-D-Gal) with a chromogenic substrate (e.g., p-nitrophenyl-β-D-galactosidase) or fluorogenic substrate (e.g., 4-methylumbelliferyl-β-D-galactosidase).

A label may be indirectly conjugated with an antibody or other reagent, as is known in the art. For example, an antibody can be conjugated with biotin and any of the types of labels mentioned above can be conjugated with avidin, or vice versa. Biotin binds selectively to avidin and thus, the label can be conjugated with the antibody in an indirect manner. In some cases, detectable labels are attached by spacer arms of various lengths to reduce potential steric hindrance.

Detection of bound, labeled antibody can be carried out by standard colorimetric, radioactive, photometric and/or fluorescent detection means. For fluorescent labels, signal can be detected by, for example, a scanning confocal microscope in photon counting mode. Appropriate scanning devices are described by, for example, U.S. Pat. Nos. 5,578,832 and 5,631,734. For antibodies labeled with biotin, the reaction can be treated with the appropriate streptavidin-conjugate (e.g., streptavidin-horseradish peroxidase, streptavidin-alkaline phosphatase, streptavidin-luciferase, and the like) and then treated with the appropriate reagents for calorimetric or photometric detection. For radiolabeled antibody, signal can be detected using a scintillation counter, phosphoimager or similar device. For reading of signals on membranes employed in a lateral flow immunochromatographic assay, a hand held scanner such as that disclosed in WO 2000/02877 may be used.

In a competitive binding assay, an isolated antigen e.g. type I collagen telopeptide, and an antibody specific to it are employed. Either of the telopeptide or the antibody is labeled with a radionuclide, enzymatic, chromogenic, or fluorescent label, or alternately a separate reagent which complexes with the antibody or telopeptide is labeled. Known techniques which may be used in the immunoassay have been described (see, e.g. "Immunochemistry of the Extracellular Matrix" H. Furthmayr, Ed., CRC Press, Inc., Boca Raton, Fla. 1982).

In an exemplary method of a competitive binding assay, labeled CTP-I and the sample are both contacted with the unlabeled antibody. The antigen-antibody complex so formed is separated from uncomplexed starting material and the complexed (or uncomplexed) label is assayed. The amount of label in the complexes is compared to the amount of label found in complexes formed in the absence of the sample i.e. wherein no competitive binding takes place. The antibody may also be bound to a solid support, whether before, during or after contacting with the sample. The resulting complex between the antibody and the CTP-I may then be separated from the medium in which the contacting takes place simply by separating the solid support from the medium.

Separation of the antigen-antibody complex may be accomplished by contacting the antigen-antibody complex with a further reagent, e.g., a second antibody specific to the first antibody and separating the antigen-antibody-antibody complex from the uncomplexed starting materials. Here again a solid support may-be employed, with the second antibody being bound to the support. Other immobilization approaches such as biotin/streptavidin complexes can also be employed.

Separation of antibody-containing complexes from the contacting medium may also be accomplished by such known methods as filtration or centrifuging.

As used herein, the term "ELISA" refers to enzyme-linked immunosorbent assay (or EIA). Numerous ELISA methods and applications are known in the art, and are described in many references (See, e.g., Crowther, "Enzyme-Linked Immunosorbent Assay (ELISA)," in Molecular Biomethods Handbook, Rapley et al. [eds.], pp. 595-617, Humana Press, Inc., Totowa, N.J. [1998]; Harlow and Lane (eds.), Antibodies: A Laboratory Manual, Cold Spring Harbor Laboratory Press [1988]; Ausubel et al. (eds.), Current Protocols in Molecular Biology, Ch. 11, John Wiley & Sons, Inc., New York [1994]). In addition, there are numerous commercially available ELISA test systems.

In accordance with the above description, ELISA methods useful in the present invention include "direct ELISA" and "indirect ELISA". In the direct technique, an enzyme-conjugated antibody specific for the antigen is used to detect antigen in the sample, whereas in the indirect technique, an unlabeled antigen-specific primary antibody and a labeled secondary antibody specific for the primary antibody. Secondary antibodies are typically "species-specific" antibodies (e.g., a goat anti-rabbit antibody), which are available from various manufacturers (e.g., Santa Cruz Biotechnology; Zymed; and Pharmingen/Transduction Laboratories).

In other embodiments, a "sandwich ELISA" is used, where the antigen is immobilized on a solid support (e.g., a microtiter plate) via an antibody (i.e., a capture antibody) that is immobilized on the solid support and is able to bind the antigen of interest. Following the affixing of a suitable capture antibody to the immobilized phase, a sample is then added to the microtiter plate well, followed by washing. If the antigen of interest is present in the sample, it is bound to the capture antibody present on the support. In some embodiments, a sandwich ELISA is a "direct sandwich" ELISA, where the captured antigen is detected directly by using an enzyme-conjugated antibody directed against the antigen. Alternatively, in other embodiments, a sandwich ELISA is an "indirect sandwich"" ELISA, where the captured antigen is detected indirectly by using an antibody directed against the antigen, which is then detected by another enzyme-conjugated antibody which binds the antigen-specific antibody, thus forming an antibody-antigen-antibody-antibody complex. Suitable reporter reagents are then added to detect the third antibody. Alternatively, in some embodiments, any number of additional antibodies is added as necessary, in order to detect the antigen-antibody complex. In some preferred embodiments, these additional antibodies are labeled or tagged, so as to permit their visualization and/or quantitation.

As used herein, the term "capture antibody" refers to an antibody that is used in a sandwich ELISA to bind (i.e., capture) an antigen in a sample prior to detection of the antigen. For example, in some embodiments, a polyclonal anti-CTP antibody serves as a capture antibody when immobilized in a microliter plate well. This capture antibody binds CTP peptide present in the blood sample added to the well. In one embodiment of the present invention, biotinylated capture antibodies are used in the present invention in conjunction with avidin-coated solid support. Another antibody (i.e., the detection antibody) is then used to bind and detect the antigen-antibody complex, in effect forming a "sandwich" comprised of antibody-antigen-antibody (i.e., a sandwich ELISA).

As used herein, a "detection antibody" is an antibody which carries a means for visualization or quantitation, which is typically a conjugated enzyme moiety, a fluorescent moiety, a radioisotope or biotin, as described above. In some embodiments, the detection antibody is directed against the antigen of interest, while in other embodiments, the detection antibody is not directed against the antigen of interest, but is an anti-species antibody directed against the antigen-specific antibody.

In preferred embodiment, the invention may be carried using a flow-through immunoassay which is a rapid immunoassay test format generally comprising a color particle coated with antibody immobilized onto a polymer membrane. Such techniques typically are based on either a sandwich-type or a competition-type assay for detecting an antigen in a sample. Exemplary devices and methods for flow-through immunoassays are disclosed in U.S. Pat. Nos. 7,090, 803; 7,238,537; 6,887,430; 6,818,456; 6,706,539; 6,485,982 and 6,394,952. In other preferred embodiments, the invention is carried out using a solid-phase chromatography immunoassay, such as that disclosed in U.S. Pat. No. 5,877,028.

The term "signal" is used generally in reference to any detectable process that indicates that a reaction has occurred, for example, binding of antibody to antigen. It is contemplated that signals in the form of radioactivity, fluorimetric or colorimetric, products/reagents will all find use with the present invention. In various embodiments of the present invention, the signal is assessed qualitatively, while in alternative embodiments, the signal is assessed quantitatively.

As used herein, the term "amplifier" is used in reference to a system which enhances the signal in an immunoassay detection method, such as an an alkaline phosphatase amplifier system used in an ELISA.

As used herein, the term "solid support" is used in reference to any solid or stationary material to which reagents such as antibodies, antigens, and other test components are attached. Examples of solid supports include microtiter plates, cell culture flasks, microscope slides, coverslips, beads, particles, polymer sheet (i.e., nitrocellulose) paper strip, silicon chips, as well as many other suitable items.

Antibody Arrays

An antibody array or microarray is a specific form of protein microarrays, in which a collection of capture antibodies are spotted and fixed on a solid substrate, such as glass, plastic or a silicon chip for the purpose of detecting antigens, preferably using an immunoassay as described above. Typically, antibodies are immobilized in a 2D addressable grid on a chip, and may contain about 100 spatially distinct antibody specificities within a total area of 1 $cm^2$.

The nature and geometry of the solid substrate will depend upon a variety of factors, including, among others, the type of array (e.g., one-dimensional, two-dimensional or three-dimensional). Generally, the surface can be composed of any material which will permit immobilization of the binding reagents and which will not substantially degrade under the conditions used in the applications of the array.

The solid substrate used for the array may be in the form of beads, particles or sheets, and may be permeable or impermeable, depending on the type of array, wherein the surface is coated with a suitable material enabling binding of the binding reagents at high affinity. For two-dimensional arrays, the solid surface may be in the form of plastic, micromachined chips, membranes, slides, plates or sheets in which at least one surface is substantially flat, wherein these surfaces may comprise glass, plastic, silicon, low cross-linked and high cross-linked polystyrene, silica gel, polyamide, and the like.

Fluorescence tagged beads are also an addressable (liquid) array in which each bead is tagged with a different set of fluorescent colors and bound with an antibody; specific to an array is detected with devices such as fluorescence scanners for arrays or FACS for beads.

Either a population of discrete antibodies is employed to form the array, such that each address presents a specificity for a different molecule i.e. skin metabolism product, or a single or a few addresses are employed with a similar antibody. In many applications, redundancies in the spots are desirable for the purposes of acting as internal controls.

Technologies for the deposition of droplets containing protein binding reagents onto a suitable solid surface are known in the art, as disclosed for example in U.S. Pat. No. 5,449,754.

In order to conduct array-based immunoassay, the test sample containing the antigen of interest is allowed to contact the array comprising a coated surface containing the anchored antibody. Following contact, the array is optionally washed, typically under conditions such that any complexes formed will remain immobilized on the solid surface and unbound material will be removed.

The detection of complexes anchored on the solid surface can be accomplished in a number of ways. In some embodiments, an indirect label can be used to detect complexes anchored on the surface; e.g., using a labeled antibody specific for the previously non-immobilized sample (the antibody, in turn, may be directly labeled or indirectly labeled with a labeled anti-Ig antibody). In another embodiment, the immobilized antibody molecules of the microarray are labeled, the array can be scanned or otherwise analyzed for detectable assay signal, and the signal from each labeled spot, or alternatively from all spots, quantified.

An important consideration is the presence of an amount of a label at each position within the array that is proportional to the amount of molecule immobilized at that particular spot. Thus, it is important that the efficiencies of the coupling reactions which are used to immobilize the labeled antibody molecules are substantially similar.

Virtually any label that produces a detectable, quantifiable signal and that is capable of being attached to an immobilized binding reagent on a substrate can be used in conjunction with the array of the invention. Suitable labels include: radioisotopes, fluorophores, chromophores, chemiluminescent moieties, as described above.

Preferably, the position of the label will not interfere with interaction between a desired sample and the immobilized antibody molecules and with the detection in case of an interaction between the desired sample and an immobilized molecule of the array. Suitable methods of making labeled molecules are well known in the art.

In the case where each spot in the array contains an amount of a label or "tracer" proportional to the amount of antibody molecules immobilized at the particular spot, the signals obtained from the arrays of the invention can be normalized. As a consequence, signal intensities from spots within a single array, or across multiple arrays, can be directly compared. A normalized signal of a particular spot may be defined by $(I_t-I_o)/I_o$, where $I_t$ is the intensity of the signal of the spot after contacting with a sample of interest and $I_o$ is the intensity of the background signal of the spot before contacting with a sample of interest.

Various methods and devices for detection and analysis of the array are known in the art. Practically, any imaging system that is capable of detecting with a resolution appropriate to the size of the array features can be utilized. For example, a method for screening an array of proteins for interactions with a fluid sample is disclosed in U.S. Pat. No. 6,475,809. Imaging apparatus for reading of signals on an antibody array may be selected, for example, from ScanArray 4000 (General Scanning), Biochip Imager (Hewlett Packard), GMS 418 Array Scanner (Genetic Microsystems), GeneTAC 1000 (Genomic Solutions), Chip Reader (Virtek), or a hand-held microanalytical instrument for example as disclosed in Renzi et al (2005) Anal Chem 77(2):435-41. Phosphorimager systems are available for detecting radiolabels, e.g. Cyclone (Packard Instrument Co.) and BAS-5000 (Fujifilm).

Antigens

Practicing the present invention requires antibodies capable of specifically identifying the proteins of the present invention, resulting from the skin degradation due to a burn. As described hereinabove, various antibodies are known in the art for collagen type I CTP, NTP, laminin and collagen type IV. Additionally or alternatively, the proteins of the present invention can be isolated or synthesized to be used as antigens for the production of specific antibodies.

Protein isolation may be carried out using methods known to a person skilled in the art. Collagen type I CTP isolation can be performed as described, for example, in U.S. Pat. Nos. 5,538,853 and 6,916,604. U.S. Pat. No. 5,354,666 describes a system of immortal mammalian cell line designated BAM for the expression and isolation of basement membrane proteins in vitro.

Cross-linked type I collagen peptides for antibody production may be obtained from human urine as described in for example in U.S. Pat. No. 5,300,434, or from human cartilage tissues, as described in for example in Eyre et al (20080 Methods 45(1):65-74.

Alternatively, the proteinaceous skin degradation product of the present invention can be synthesized using any recombinant or synthetic method known in the art, including, but not limited to, solid phase (e.g. Boc or f-Moc chemistry) and solution phase synthesis methods. For solid phase peptide synthesis, a summary of the many techniques may be found in Stewart and Young, 1963 (Prog Med Chem. 19, 187-260); and Meienhofer and Atherton 1973 (Adv Appl Microbiol, 16, 203-300). For a review of classical solution synthesis, see Schroder and Lupke, 1965 (The Peptides, Vol. 1, Academic Press (New York).

Antibodies

As used herein, the term "antibody" refers to a substantially intact antibody molecule.

As used herein, the phrase "antibody fragment" refers to a functional fragment of an antibody that is capable of binding to an antigen.

Suitable antibody fragments for practicing the present invention include, inter alia, a complementarity-determining region (CDR) of an immunoglobulin light chain (referred to herein as "light chain"), a CDR of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single-chain Fv, an Fab, an Fab', and an F(ab')2.

Functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single-chain Fv ("scFv"), a genetically engineered single-chain molecule including the variable region of the light chain and the variable region of the heavy chain, linked by a suitable polypeptide linker.

(iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof;

(iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

Methods of generating monoclonal and polyclonal antibodies are well known in the art. Antibodies may be generated via any one of several known methods, which may employ induction of in vivo production of antibody molecules, screening of immunoglobulin libraries (Orlandi, R. et al. (1989). Proc Natl Acad Sci USA 86, 3833-3837; and Winter, G. and Milstein, C. (1991). Nature 349, 293-299), or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler, G. and Milstein, C. (1975). Nature 256, 495-497; Kozbor, D. et al. (1985). J Immunol Methods 81, 31-42; Cote R J. et al. (1983). Proc Natl. Acad Sci USA 80, 2026-2030; and Cole, S. P. et al. (1984). Mol Cell Biol 62, 109-120).

In cases where target antigens are too small to elicit an adequate immunogenic response when generating antibodies in vivo, such antigens (referred to as "haptens") can be coupled to antigenically neutral carriers such as keyhole limpet hemocyanin (KLH) or serum albumin (e.g., bovine serum albumin (BSA)) carriers (see, for example, U.S. Pat. Nos. 5,189,178 and 5,239,078). Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill., USA. The resulting immunogenic complex can then be injected into suitable mammalian subjects such as mice, rabbits, and others. Suitable protocols involve repeated injection of the immunogen in the presence of adjuvants according to a schedule designed to boost production of antibodies in the serum. The titers of the immune serum can readily be measured using immunoassay procedures which are well known in the art.

The antisera obtained can be used directly or monoclonal antibodies may be obtained, as described hereinabove.

Antibody fragments may be obtained using methods well known in the art. (See, for example, Harlow, E. and Lane, D. (1988). Antibodies: A Laboratory Manual, Cold Spring Harbor Laboratory, New York.) For example, antibody fragments according to the present invention can be prepared by proteolytic hydrolysis of the antibody or by expression in E. coli or mammalian cells (e.g., Chinese hamster ovary (CHO) cell culture or other protein expression systems) of DNA encoding the fragment.

Alternatively, antibody fragments can be obtained by pepsin or papain digestion of whole antibodies by conventional methods. As described hereinabove, an (Fab')2 antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: U.S. Pat. Nos. 4,036,945 and 4,331,647; and Porter, R. R. (1959). Biochem J 73, 119-126). Other methods of cleaving antibodies, such as separation of heavy chains to form monovalent light-heavy chain fragments, further cleavage of fragments, or other enzymatic, chemical, or genetic techniques may also be used, so long as the fragments retain the ability to bind to the antigen that is recognized by the intact antibody.

As described hereinabove, an Fv is composed of paired heavy chain variable and light chain variable domains. This association may be noncovalent (see, for example, Inbar, D. et al. (1972). Proc Natl Acad Sci USA 69, 2659-2662). Alternatively, as described hereinabove, the variable domains may be linked to generate a single-chain Fv by an intermolecular disulfide bond, or alternately such chains may be cross-linked by chemicals such as glutaraldehyde.

Preferably, the Fv is a single-chain Fv. Single-chain Fvs are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as E. coli. The recombinant host cells synthesize a single polypeptide chain with a linker peptide bridging the two variable domains. Ample guidance for producing single-chain Fvs is provided in the literature of the art (see, e.g.: Whitlow, M. and Filpula, D. (1991). Single-chain Fv proteins and their fusion proteins. METHODS: A Companion to Methods in Enzymology 2(2), 97-105; Bird, R. E. et al. (1988). Science 242, 423-426; Pack, P. et al. (1993). Improved bivalent miniantibodies, with identical avidity as whole antibodies, produced by high cell density fermentation of Escherichia coli. Biotechnology (N.Y.) 11(11), 1271-1277; and U.S. Pat. No. 4,946,778).

Isolated complementarity-determining region peptides can be obtained by constructing genes encoding the CDR of an antibody of interest. Such genes may be prepared, for example, by RT-PCR of the mRNA of an antibody-producing cell. Ample guidance for practicing such methods is provided in the literature of the art (e.g., Larrick, J. W. and Fry, K. E. (1991). PCR Amplification of Antibody Genes. METHODS: A Companion to Methods in Enzymology 2(2), 106-110).

Kits

The invention also includes kits for detecting a skin degradation product in a fluid biological sample. The kit may be used for determining the severity of a burn in a subject. The kit comprises a container, a sample tube, or the like, for storing the fluid biological sample, such as blood or urine, obtained from the subject.

The kit also comprises one or more detection reagents which specifically bind with selected skin degradation products as described herein. The detection reagents are present in the kit in an amount effective to permit detection of the protein(s) of interest. Detection of the proteins is accomplished using any of the methods described herein or known to a skilled artisan for detecting a specific protein within a biological fluid sample.

The kit also comprises an instructional material which directs the use of the reagents and the sample for the function of determining the amount of the proteins in the sample. The instructional material also directs the correlation of the amount of the protein in the sample with a reference level for determining the severity of the burn in the subject, and for determining a parameter such as the percentage of body surface area affected with each degree of burn severity or the depth of the burn.

In particular embodiments, the detection reagent is specific for a collagen type IV, such as that comprising SEQ ID NO:24; SEQ ID NO:25; SEQ ID NO:26; SEQ ID NO:27; SEQ ID NO:28; SEQ ID NO:29 or SEQ ID NO:30.

As used herein, an "instructional material" includes a publication, a recording, a diagram, or any other medium of expression which directs or dictates the use of the components of a kit for performing the function of a method of the invention described herein. The instructional material of the kit of the invention may, for example, be affixed to a container which contains the composition or be shipped together with a container which contains the composition.

The following examples are presented in order to more fully illustrate the preferred embodiments of the invention. They should in no way be construed, however, as limiting the broad scope of the invention.

EXAMPLES

Example 1

C-telopeptide Concentration in Control and Post-Burn Samples

A guinea pig model of burn injury is used. The animals are exposed to heat trauma using the following protocol: A guinea pig is shaved (electrical shaver) twenty-four hours prior the experiment. After shaving, the animal is anesthetized by 15-30 mg/kg pentobarbital i.p., placed in insulating fixed area shield, dorsum exposed, and immersed in a water bath of 80° C. for 30 sec. This produces a full-thickness burn, of about 25% of body surface area. Animal are then immediately resuscitated post-burn with 3 ml i.p. of sterile normal saline.

Blood samples are obtained from the anesthetized animals before the exposure to heat (time 0, control) and at 15, 30, 60 and 120 min post-burn. At least four samples for each time point are taken. Concentration of C-telopeptide is assessed using radio-immunoassay and anti-C-telopeptide antibody (Orion Diagnostica (Espoo, Finland). This model shows that the CTP concentration in a blood sample taken from a guinea pig having a full-thickness burn at about 25% of its body surface area is significantly higher compared to its concentration in blood taken from the same animal before burn is induced.

Example 2

Figure 2:
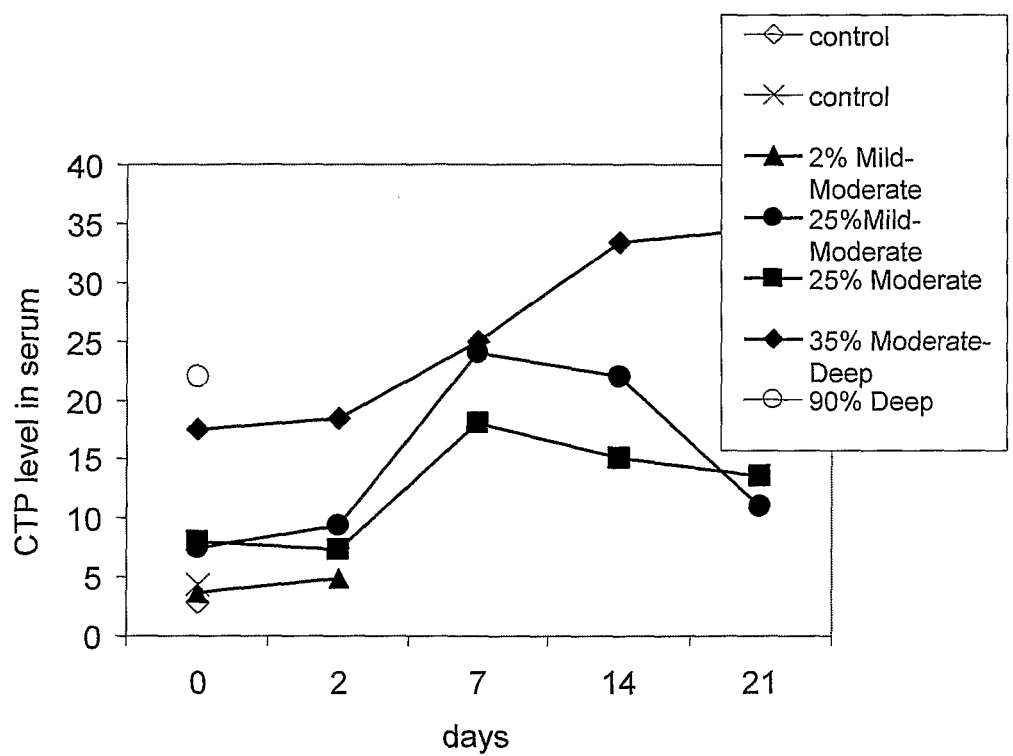
FIG. 2 shows CTP levels in patient blood samples collected at day 0, and at 48, 84 and 168 hours following burn injury.

Use of the Concentration of CTP-I in Blood Samples for Assessment of Burn Injury Severity This preliminary study included 5 burn patients, each of which had a differing degree of burn severity and percentage of body area affected as follows: patient 1: mild, 2% body area; patient 2: mild-moderate, 25% body area; patient 3: moderate, 25% body area; patient 4: moderate-deep, 35% body area, and patient 5: deep, 90% body area). Four healthy individuals served as a control group. Blood samples were taken from patients on arrival to the hospital emergency room, or within 3 hours of arrival. CTP-I serum levels were measured using ELISA and anti-C-telopeptide antibody (UniQ). As shown in FIG. 1, the CTP-I levels of patients 1-5 were respectively 4.8 (empty bars); 6.95 (horizontally striped bars); 8.02 (diagonally striped bars); 18.48 (stippled bars); and 23.49 (vertically striped bars) ng per L, respectively. The CTP-I levels of the control group (black bars) were: 2.85, 4.42, 3.74, and 3.74 ng per L, respectively.

These results show that the CTP-I levels in the burn patients were significantly increased over that in the control group, and moreover, the levels of CTP-1 in the patients showed significant correlation with burn severity and the percentage of body area affected.

Example 3

Measuring Dynamics of CTP-I Serum Levels for Monitoring of Burn Patients

The patients described in Example 2 were continually monitored at periodic intervals (corresponding to 2, 7, 14 and 21 days following burn injury) for CTP-I levels in blood. The results, shown in FIG. 2, indicate that in some patients, the level of CTP-I declined as the burn injury healing process proceeded.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A kit for determining the severity of a burn, the kit comprising
    (a) at least one antibody reagent suitable for detecting the level of at least one skin catabolism product in a biological fluid sample from a subject, wherein the skin catabolism product is carboxy terminal telopeptide of type I collagen (CTP-I) and the biological fluid sample is obtained from a subject affected with a burn within 24 hours from the time when the subject sustained the burn injury; and
    (b) instructional material directing the correlation of the detected level of the CTP-1 in the sample with a reference level that corresponds to a particular degree of burn severity.

2. The kit according to claim 1, wherein the reference level of the burn severity comprises at least one parameter selected from the group consisting of: the percentage of body surface area affected with a particular degree of burn, and the depth of a burn.

3. The kit according to claim 1, wherein the biological fluid sample is selected from the group consisting of blood, plasma, serum and urine.

4. The kit according to claim 1, wherein the at least one antibody reagent is specific for carboxy terminal telopeptide of type I collagen (CTP-I) selected from the group consisting of SEQ ID NO:1; SEQ ID NO:4; SEQ ID NO:5 and SEQ ID NO:6.

* * * * *

SEQUENCE LISTING

```
<160> NUMBER OF SEQ ID NOS: 30

<210> SEQ ID NO 1
<211> LENGTH: 29
<212> TYPE: PRT
<213> ORGANISM: Homo sapiens
<220> FEATURE:
<221> NAME/KEY: MISC_FEATURE
```

```
<222> LOCATION: (3)..(3)
<223> OTHER INFORMATION: Xaa is hydroxyproline

<400> SEQUENCE: 1

Gly Pro Xaa Ser Ala Gly Phe Asp Phe Ser Phe Leu Pro Gln Pro Pro
1               5                   10                  15

Glu Glu Lys Ala His Asp Gly Gly Arg Tyr Tyr Arg Ala
            20                  25

<210> SEQ ID NO 2
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: Sequence is part of cross-linked peptide
<220> FEATURE:
<221> NAME/KEY: MISC_FEATURE
<222> LOCATION: (3)..(3)
<223> OTHER INFORMATION: Xaa is hydroxyproline
<220> FEATURE:
<221> NAME/KEY: MISC_FEATURE
<222> LOCATION: (9)..(9)
<223> OTHER INFORMATION: Xaa is hydroxyproline
<220> FEATURE:
<221> NAME/KEY: MISC_FEATURE
<222> LOCATION: (12)..(12)
<223> OTHER INFORMATION: Xaa is hydroxylysine

<400> SEQUENCE: 2

Gly Leu Xaa Gly Thr Ala Gly Leu Xaa Gly Met Xaa Gly His Arg
1               5                   10                  15

<210> SEQ ID NO 3
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: Sequence is part of cross-linked peptide
<220> FEATURE:
<221> NAME/KEY: MISC_FEATURE
<222> LOCATION: (3)..(3)
<223> OTHER INFORMATION: Xaa is hydroxyproline
<220> FEATURE:
<221> NAME/KEY: MISC_FEATURE
<222> LOCATION: (6)..(6)
<223> OTHER INFORMATION: Xaa is hydroxyproline
<220> FEATURE:
<221> NAME/KEY: MISC_FEATURE
<222> LOCATION: (9)..(9)
<223> OTHER INFORMATION: Xaa is hydroxyproline
<220> FEATURE:
<221> NAME/KEY: MISC_FEATURE
<222> LOCATION: (12)..(12)
<223> OTHER INFORMATION: Xaa is hydroxylysine

<400> SEQUENCE: 3

Gly Phe Xaa Gly Thr Xaa Gly Leu Xaa Gly Phe Xaa Gly Ile Arg
1               5                   10                  15

<210> SEQ ID NO 4
<211> LENGTH: 18
<212> TYPE: PRT
<213> ORGANISM: Homo sapiens

<400> SEQUENCE: 4

Asp Phe Ser Phe Leu Pro Gln Pro Pro Gln Glu Lys Ala His Asp Gly
1               5                   10                  15
```

Gly Arg

<210> SEQ ID NO 5
<211> LENGTH: 25
<212> TYPE: PRT
<213> ORGANISM: Homo sapiens

<400> SEQUENCE: 5

Ser Ala Gly Phe Asp Phe Ser Phe Leu Pro Gln Pro Pro Gln Glu Lys
1               5                   10                  15

His Asp Gly Gly Arg Tyr Tyr Arg Ala
            20                  25

<210> SEQ ID NO 6
<211> LENGTH: 12
<212> TYPE: PRT
<213> ORGANISM: Homo sapiens

<400> SEQUENCE: 6

Tyr Asp Phe Gly Tyr Asp Gly Asp Phe Tyr Arg Ala
1               5                   10

<210> SEQ ID NO 7
<211> LENGTH: 16
<212> TYPE: PRT
<213> ORGANISM: Homo sapiens

<400> SEQUENCE: 7

Gln Leu Ser Tyr Gly Tyr Asp Glu Lys Ser Thr Gly Gly Ile Ser Val
1               5                   10                  15

<210> SEQ ID NO 8
<211> LENGTH: 8
<212> TYPE: PRT
<213> ORGANISM: Homo sapiens

<400> SEQUENCE: 8

Gln Tyr Asp Gly Lys Gly Val Gly
1               5

<210> SEQ ID NO 9
<211> LENGTH: 11
<212> TYPE: PRT
<213> ORGANISM: Homo sapiens

<400> SEQUENCE: 9

Gln Tyr Asp Gly Lys Gly Val Gly Leu Gly Pro
1               5                   10

<210> SEQ ID NO 10
<211> LENGTH: 6
<212> TYPE: PRT
<213> ORGANISM: Homo sapiens

<400> SEQUENCE: 10

Glu Lys Gly Pro Asp Pro
1               5

<210> SEQ ID NO 11
<211> LENGTH: 24
<212> TYPE: PRT
<213> ORGANISM: Homo sapiens

<400> SEQUENCE: 11

```
Ile Asp Met Ser Ala Phe Ala Gly Leu Gly Pro Arg Glu Lys Gly Pro
1               5                   10                  15

Asp Pro Leu Gln Tyr Met Arg Ala
            20

<210> SEQ ID NO 12
<211> LENGTH: 19
<212> TYPE: PRT
<213> ORGANISM: Homo sapiens

<400> SEQUENCE: 12

Gln Met Ala Gly Gly Phe Asp Glu Lys Ala Gly Gly Ala Gln Leu Gly
1               5                   10                  15

Val Met Gln

<210> SEQ ID NO 13
<211> LENGTH: 24
<212> TYPE: PRT
<213> ORGANISM: Homo sapiens

<400> SEQUENCE: 13

Cys Gly Gly Val Gly Ala Ala Ala Ile Ala Gly Ile Gly Gly Glu Lys
1               5                   10                  15

Gly Gly Phe Ala Pro Tyr Tyr Gly
            20

<210> SEQ ID NO 14
<211> LENGTH: 14
<212> TYPE: PRT
<213> ORGANISM: Homo sapiens

<400> SEQUENCE: 14

Gln Tyr Asp Ser Tyr Asp Val Lys Ser Gly Val Ala Val Gly
1               5                   10

<210> SEQ ID NO 15
<211> LENGTH: 246
<212> TYPE: PRT
<213> ORGANISM: Homo sapiens

<400> SEQUENCE: 15

Asp Asp Ala Asn Val Val Arg Asp Arg Asp Leu Glu Val Asp Thr Thr
1               5                   10                  15

Leu Lys Ser Leu Ser Gln Gln Ile Glu Asn Ile Arg Ser Pro Glu Gly
            20                  25                  30

Ser Arg Lys Asn Pro Ala Arg Thr Cys Arg Asp Leu Lys Met Cys His
        35                  40                  45

Ser Asp Trp Lys Ser Gly Glu Tyr Trp Ile Asp Pro Asn Gln Gly Cys
    50                  55                  60

Asn Leu Asp Ala Ile Lys Val Phe Cys Asn Met Glu Thr Gly Glu Thr
65                  70                  75                  80

Cys Val Tyr Pro Thr Gln Pro Ser Val Ala Gln Lys Asn Trp Tyr Ile
                85                  90                  95

Ser Lys Asn Pro Lys Asp Lys Arg His Val Trp Phe Gly Glu Ser Met
            100                 105                 110

Thr Asp Gly Phe Gln Phe Glu Tyr Gly Gly Gln Gly Ser Asp Pro Ala
        115                 120                 125

Asp Val Ala Ile Gln Leu Thr Phe Leu Arg Leu Met Ser Thr Glu Ala
    130                 135                 140
```

```
Ser Gln Asn Ile Thr Tyr His Cys Lys Asn Ser Val Ala Tyr Met Asp
145                 150                 155                 160

Gln Gln Thr Gly Asn Leu Lys Lys Ala Leu Leu Lys Gly Ser Asn
            165                 170                 175

Glu Ile Glu Ile Arg Ala Glu Gly Asn Ser Arg Phe Thr Tyr Ser Val
            180                 185                 190

Thr Val Asp Gly Cys Thr Ser His Thr Gly Ala Trp Gly Lys Thr Val
            195                 200                 205

Ile Glu Tyr Lys Thr Thr Lys Thr Ser Arg Leu Pro Ile Ile Asp Val
            210                 215                 220

Ala Pro Leu Asp Val Gly Ala Pro Asp Gln Glu Phe Gly Phe Asp Val
225                 230                 235                 240

Gly Pro Val Cys Phe Leu
                245
```

<210> SEQ ID NO 16
<211> LENGTH: 139
<212> TYPE: PRT
<213> ORGANISM: Homo sapiens

<400> SEQUENCE: 16

```
Gln Glu Glu Gly Gln Val Gly Gln Asp Glu Asp Ile Pro Pro Ile
1               5                   10                  15

Thr Cys Val Gln Asn Gly Leu Arg Tyr His Asp Arg Asp Val Trp Lys
                20                  25                  30

Pro Glu Pro Cys Arg Ile Cys Val Cys Asp Asn Gly Lys Val Leu Cys
            35                  40                  45

Asp Asp Val Ile Cys Asp Glu Thr Lys Asn Cys Pro Gly Ala Glu Val
        50                  55                  60

Pro Glu Gly Glu Cys Cys Pro Val Cys Pro Asp Gly Ser Glu Ser Pro
65                  70                  75                  80

Thr Asp Gln Glu Thr Thr Gly Val Glu Gly Pro Lys Gly Asp Thr Gly
                85                  90                  95

Pro Arg Gly Pro Arg Gly Pro Ala Gly Pro Pro Gly Arg Asp Gly Ile
            100                 105                 110

Pro Gly Gln Pro Gly Leu Pro Gly Pro Pro Gly Pro Pro Gly Pro Pro
        115                 120                 125

Gly Pro Pro Gly Leu Gly Gly Asn Phe Ala Pro
            130                 135
```

<210> SEQ ID NO 17
<211> LENGTH: 265
<212> TYPE: PRT
<213> ORGANISM: Homo sapiens

<400> SEQUENCE: 17

```
Gly Val Ser Gly Gly Gly Tyr Asp Phe Gly Tyr Asp Gly Asp Phe Tyr
1               5                   10                  15

Arg Ala Asp Gln Pro Arg Ser Ala Pro Ser Leu Arg Pro Lys Asp Tyr
                20                  25                  30

Glu Val Asp Ala Thr Leu Lys Ser Leu Asn Asn Gln Ile Glu Thr Leu
            35                  40                  45

Leu Thr Pro Glu Gly Ser Arg Lys Asn Pro Ala Arg Thr Cys Arg Asp
        50                  55                  60

Leu Arg Leu Ser His Pro Glu Trp Ser Ser Gly Tyr Tyr Trp Ile Asp
65                  70                  75                  80
```

```
Pro Asn Gln Gly Cys Thr Met Glu Ala Ile Lys Val Tyr Cys Asp Phe
                85                  90                  95
Pro Thr Gly Glu Thr Cys Ile Arg Ala Gln Pro Glu Asn Ile Pro Ala
           100                 105                 110
Lys Asn Trp Tyr Arg Ser Ser Lys Asp Lys Lys His Val Trp Leu Gly
       115                 120                 125
Glu Thr Ile Asn Ala Gly Ser Gln Phe Glu Tyr Asn Val Glu Gly Val
   130                 135                 140
Thr Ser Lys Glu Met Ala Thr Gln Leu Ala Phe Met Arg Leu Leu Ala
145                 150                 155                 160
Asn Tyr Ala Ser Gln Asn Ile Thr Tyr His Cys Lys Asn Ser Ile Ala
               165                 170                 175
Tyr Met Asp Glu Glu Thr Gly Asn Leu Lys Lys Ala Val Ile Leu Gln
           180                 185                 190
Gly Ser Asn Asp Val Glu Leu Val Ala Glu Gly Asn Ser Arg Phe Thr
       195                 200                 205
Tyr Thr Val Leu Val Asp Gly Cys Ser Lys Lys Thr Asn Glu Trp Gly
   210                 215                 220
Lys Thr Ile Ile Glu Tyr Lys Thr Asn Lys Pro Ser Arg Leu Pro Phe
225                 230                 235                 240
Leu Asp Ile Ala Pro Leu Asp Ile Gly Gly Ala Asp His Glu Phe Phe
               245                 250                 255
Val Asp Ile Gly Pro Val Cys Phe Lys
           260                 265

<210> SEQ ID NO 18
<211> LENGTH: 55
<212> TYPE: PRT
<213> ORGANISM: Homo sapiens

<400> SEQUENCE: 18

Leu Gln Glu Glu Thr Val Arg Lys Gly Pro Ala Gly Asp Arg Gly Pro
1               5                   10                  15
Arg Gly Glu Arg Gly Pro Pro Gly Pro Pro Gly Arg Asp Gly Glu Asp
            20                  25                  30
Gly Pro Thr Gly Pro Pro Gly Pro Pro Gly Pro Pro Gly Pro Pro Gly
        35                  40                  45
Leu Gly Gly Asn Phe Ala Ala
    50                  55

<210> SEQ ID NO 19
<211> LENGTH: 7
<212> TYPE: PRT
<213> ORGANISM: Homo sapiens

<400> SEQUENCE: 19

Asp Glu Lys Ser Thr Gly Gly
1               5

<210> SEQ ID NO 20
<211> LENGTH: 6
<212> TYPE: PRT
<213> ORGANISM: Homo sapiens

<400> SEQUENCE: 20

Asp Gly Gln Lys Gly Ala
1               5
```

-continued

<210> SEQ ID NO 21
<211> LENGTH: 4
<212> TYPE: PRT
<213> ORGANISM: Homo sapiens

<400> SEQUENCE: 21

Lys Glu Gly Gln
1

<210> SEQ ID NO 22
<211> LENGTH: 8
<212> TYPE: PRT
<213> ORGANISM: Homo sapiens

<400> SEQUENCE: 22

Gly Asp Ala Gly Ala Lys Gly Asp
1               5

<210> SEQ ID NO 23
<211> LENGTH: 8
<212> TYPE: PRT
<213> ORGANISM: Homo sapiens

<400> SEQUENCE: 23

Glu Lys Ala His Asp Gly Gly Arg
1               5

<210> SEQ ID NO 24
<211> LENGTH: 260
<212> TYPE: PRT
<213> ORGANISM: Homo sapiens

<400> SEQUENCE: 24

Met Arg Ala Trp Ile Phe Phe Leu Leu Cys Leu Ala Gly Arg Ala Leu
1               5                   10                  15

Ala Ala Pro Leu Ala Asp Tyr Lys Asp Asp Asp Lys Leu Ala Ser
            20                  25                  30

Val Asp His Gly Phe Leu Val Thr Arg His Ser Gln Thr Ile Asp Asp
        35                  40                  45

Pro Gln Cys Pro Ser Gly Thr Lys Ile Leu Tyr His Gly Tyr Ser Leu
    50                  55                  60

Leu Tyr Val Gln Gly Asn Glu Arg Ala His Gly Gln Asp Leu Gly Thr
65                  70                  75                  80

Ala Gly Ser Cys Leu Arg Lys Phe Ser Thr Met Pro Phe Leu Phe Cys
                85                  90                  95

Asn Ile Asn Asn Val Cys Asn Phe Ala Ser Arg Asn Asp Tyr Ser Tyr
            100                 105                 110

Trp Leu Ser Thr Pro Glu Pro Met Pro Met Ser Met Ala Pro Ile Thr
        115                 120                 125

Gly Glu Asn Ile Arg Pro Phe Ile Ser Arg Cys Ala Val Cys Glu Ala
    130                 135                 140

Pro Ala Met Val Met Ala Val His Ser Gln Thr Ile Gln Ile Pro Pro
145                 150                 155                 160

Cys Pro Ser Gly Trp Ser Ser Leu Trp Ile Gly Tyr Ser Phe Val Met
                165                 170                 175

His Thr Ser Ala Gly Ala Glu Gly Ser Gly Gln Ala Leu Ala Ser Pro
            180                 185                 190

Gly Ser Cys Leu Glu Glu Phe Arg Ser Ala Pro Phe Ile Glu Cys His
        195                 200                 205

Gly Arg Gly Thr Cys Asn Tyr Tyr Ala Asn Ala Tyr Ser Phe Trp Leu
            210                 215                 220

Ala Thr Ile Glu Arg Ser Glu Met Phe Lys Lys Pro Thr Pro Ser Thr
225                 230                 235                 240

Leu Lys Ala Gly Glu Leu Arg Thr His Val Ser Arg Cys Gln Val Cys
                245                 250                 255

Met Arg Arg Thr
            260

<210> SEQ ID NO 25
<211> LENGTH: 258
<212> TYPE: PRT
<213> ORGANISM: Homo sapiens

<400> SEQUENCE: 25

Met Arg Ala Trp Ile Phe Phe Leu Leu Cys Leu Ala Gly Arg Ala Leu
1               5                   10                  15

Ala Ala Pro Leu Ala Asp Tyr Lys Asp Asp Asp Lys Leu Ala Val
            20                  25                  30

Ser Ile Gly Tyr Leu Leu Val Lys His Ser Gln Thr Asp Gln Glu Pro
            35                  40                  45

Met Cys Pro Val Gly Met Asn Lys Leu Trp Ser Gly Tyr Ser Leu Leu
50                  55                  60

Tyr Phe Glu Gly Gln Glu Lys Ala His Asn Gln Asp Leu Gly Leu Ala
65                  70                  75                  80

Gly Ser Cys Leu Ala Arg Phe Ser Thr Met Pro Phe Leu Tyr Cys Asn
                85                  90                  95

Pro Gly Asp Val Cys Tyr Tyr Ala Ser Arg Asn Asp Lys Ser Tyr Trp
                100                 105                 110

Leu Ser Thr Thr Ala Pro Leu Pro Met Met Pro Val Ala Glu Asp Glu
            115                 120                 125

Ile Lys Pro Tyr Ile Ser Arg Cys Ser Val Cys Glu Ala Pro Ala Ile
130                 135                 140

Ala Ile Ala Val His Ser Gln Asp Val Ser Ile Pro His Cys Pro Ala
145                 150                 155                 160

Gly Trp Arg Ser Leu Trp Ile Gly Tyr Ser Phe Leu Met His Thr Ala
                165                 170                 175

Ala Gly Asp Glu Gly Gly Gly Gln Ser Leu Val Ser Pro Gly Ser Cys
            180                 185                 190

Leu Glu Asp Phe Arg Ala Thr Pro Phe Ile Glu Cys Asn Gly Gly Arg
            195                 200                 205

Gly Thr Cys His Tyr Tyr Ala Asn Lys Tyr Ser Phe Trp Leu Thr Thr
            210                 215                 220

Ile Pro Glu Gln Ser Phe Gln Gly Ser Pro Ser Ala Asp Thr Leu Lys
225                 230                 235                 240

Ala Gly Leu Ile Arg Thr His Ile Ser Arg Cys Gln Val Cys Met Lys
                245                 250                 255

Asn Leu

<210> SEQ ID NO 26
<211> LENGTH: 268
<212> TYPE: PRT
<213> ORGANISM: Homo sapiens

<400> SEQUENCE: 26

Met Arg Ala Trp Ile Phe Phe Leu Leu Cys Leu Ala Gly Arg Ala Leu
1               5                   10                  15

Ala Ala Pro Leu Ala Asp Tyr Lys Asp Asp Asp Lys Arg Gly Asp
            20                  25                  30

Ser Gly Ser Pro Ala Thr Trp Thr Thr Arg Gly Phe Val Phe Thr Arg
        35                  40                  45

His Ser Gln Thr Thr Ala Ile Pro Ser Cys Pro Glu Gly Thr Val Pro
50                  55                  60

Leu Tyr Ser Gly Phe Ser Phe Leu Phe Val Gln Gly Asn Gln Arg Ala
65                  70                  75                  80

His Gly Gln Asp Leu Gly Thr Leu Gly Ser Cys Leu Gln Arg Phe Thr
                85                  90                  95

Thr Met Pro Phe Leu Phe Cys Asn Val Asn Asp Val Cys Asn Phe Ala
                100                 105                 110

Ser Arg Asn Asp Tyr Ser Tyr Trp Leu Ser Thr Pro Ala Leu Met Pro
            115                 120                 125

Met Asn Met Ala Pro Ile Thr Gly Arg Ala Leu Glu Pro Tyr Ile Ser
        130                 135                 140

Arg Cys Thr Val Cys Glu Gly Pro Ala Ile Ala Ile Ala Val His Ser
145                 150                 155                 160

Gln Thr Thr Asp Ile Pro Pro Cys Pro His Gly Trp Ile Ser Leu Trp
                165                 170                 175

Lys Gly Phe Ser Phe Ile Met Phe Thr Ser Ala Gly Ser Glu Gly Ala
                180                 185                 190

Gly Gln Ala Leu Ala Ser Pro Gly Ser Cys Leu Glu Glu Phe Arg Ala
            195                 200                 205

Ser Pro Phe Leu Glu Cys His Gly Arg Gly Thr Cys Asn Tyr Tyr Ser
        210                 215                 220

Asn Ser Tyr Ser Phe Trp Leu Ala Ser Leu Asn Pro Glu Arg Met Phe
225                 230                 235                 240

Arg Lys Pro Ile Pro Ser Thr Val Lys Ala Gly Glu Leu Glu Lys Ile
                245                 250                 255

Ile Ser Arg Cys Gln Val Cys Met Lys Lys Arg His
            260                 265

<210> SEQ ID NO 27
<211> LENGTH: 260
<212> TYPE: PRT
<213> ORGANISM: Homo sapiens

<400> SEQUENCE: 27

Met Arg Ala Trp Ile Phe Phe Leu Leu Cys Leu Ala Gly Arg Ala Leu
1               5                   10                  15

Ala Ala Pro Leu Ala Asp Tyr Lys Asp Asp Asp Lys Pro Gly Tyr
            20                  25                  30

Leu Gly Gly Phe Leu Leu Val Leu His Ser Gln Thr Asp Gln Glu Pro
        35                  40                  45

Thr Cys Pro Leu Gly Met Pro Arg Leu Trp Thr Gly Tyr Ser Leu Leu
50                  55                  60

Tyr Leu Glu Gly Gln Glu Lys Ala His Asn Gln Asp Leu Gly Leu Ala
65                  70                  75                  80

Gly Ser Cys Leu Pro Val Phe Ser Thr Leu Pro Phe Ala Tyr Cys Asn
                85                  90                  95

Ile His Gln Val Cys His Tyr Ala Gln Arg Asn Asp Arg Ser Tyr Trp
                100                 105                 110

```
Leu Ala Ser Ala Ala Pro Leu Pro Met Met Pro Leu Ser Glu Glu Ala
            115                 120                 125

Ile Arg Pro Tyr Val Ser Arg Cys Ala Val Cys Glu Ala Pro Ala Gln
130                 135                 140

Ala Val Ala Val His Ser Gln Asp Gln Ser Ile Pro Pro Cys Pro Gln
145                 150                 155                 160

Thr Trp Arg Ser Leu Trp Ile Gly Tyr Ser Phe Leu Met His Thr Gly
            165                 170                 175

Ala Gly Asp Gln Gly Gly Gln Ala Leu Met Ser Pro Gly Ser Cys
            180                 185                 190

Leu Glu Asp Phe Arg Ala Ala Pro Phe Leu Glu Cys Gln Gly Arg Gln
            195                 200                 205

Gly Thr Cys His Phe Phe Ala Asn Lys Tyr Ser Phe Trp Leu Thr Thr
            210                 215                 220

Val Lys Ala Asp Leu Gln Phe Ser Ser Ala Pro Ala Pro Asp Thr Leu
225                 230                 235                 240

Lys Glu Ser Gln Ala Gln Arg Gln Lys Ile Ser Arg Cys Gln Val Cys
            245                 250                 255

Val Lys Tyr Ser
            260

<210> SEQ ID NO 28
<211> LENGTH: 264
<212> TYPE: PRT
<213> ORGANISM: Homo sapiens

<400> SEQUENCE: 28

Met Arg Ala Trp Ile Phe Phe Leu Leu Cys Leu Ala Gly Arg Ala Leu
1               5                   10                  15

Ala Ala Pro Leu Ala Asp Tyr Lys Asp Asp Asp Lys Gly Pro Pro
            20                  25                  30

Gly Thr Ser Ser Val Ala His Gly Phe Leu Ile Thr Arg His Ser Gln
            35                  40                  45

Thr Thr Asp Ala Pro Gln Cys Pro Gln Gly Thr Leu Gln Val Tyr Glu
50                  55                  60

Gly Phe Ser Leu Leu Tyr Val Gln Gly Asn Lys Arg Ala His Gly Gln
65                  70                  75                  80

Asp Leu Gly Thr Ala Gly Ser Cys Leu Arg Arg Phe Ser Thr Met Pro
            85                  90                  95

Phe Met Phe Cys Asn Ile Asn Asn Val Cys Asn Phe Ala Ser Arg Asn
            100                 105                 110

Asp Tyr Ser Tyr Trp Leu Ser Thr Pro Glu Pro Met Pro Met Ser Met
            115                 120                 125

Gln Pro Leu Lys Gly Gln Ser Ile Gln Pro Phe Ile Ser Arg Cys Ala
130                 135                 140

Val Cys Glu Ala Pro Ala Val Val Ile Ala Val His Ser Gln Thr Ile
145                 150                 155                 160

Gln Ile Pro His Cys Pro Gln Gly Trp Asp Ser Leu Trp Ile Gly Tyr
            165                 170                 175

Ser Phe Met Met His Thr Ser Ala Gly Ala Glu Gly Ser Gly Gln Ala
            180                 185                 190

Leu Ala Ser Pro Gly Ser Cys Leu Glu Glu Phe Arg Ser Ala Pro Phe
            195                 200                 205

Ile Glu Cys His Gly Arg Gly Thr Cys Asn Tyr Tyr Ala Asn Ser Tyr
```

```
                210                 215                 220
Ser Phe Trp Leu Ala Thr Val Asp Val Ser Asp Met Phe Ser Lys Pro
225                 230                 235                 240

Gln Ser Glu Thr Leu Lys Ala Gly Asp Leu Arg Thr Arg Ile Ser Arg
            245                 250                 255

Cys Gln Val Cys Met Lys Arg Thr
            260

<210> SEQ ID NO 29
<211> LENGTH: 260
<212> TYPE: PRT
<213> ORGANISM: Homo sapiens

<400> SEQUENCE: 29

Met Arg Ala Trp Ile Phe Phe Leu Leu Cys Leu Ala Gly Arg Ala Leu
1               5                   10                  15

Ala Ala Pro Leu Ala Asp Tyr Lys Asp Asp Asp Lys Leu Ala Ser
            20                  25                  30

Met Arg Val Gly Tyr Thr Leu Val Lys His Ser Gln Ser Glu Gln Val
            35                  40                  45

Pro Pro Cys Pro Ile Gly Met Ser Gln Leu Trp Val Gly Tyr Ser Leu
50                  55                  60

Leu Phe Val Glu Gly Gln Glu Lys Ala His Asn Gln Asp Leu Gly Phe
65                  70                  75                  80

Ala Gly Ser Cys Leu Pro Arg Phe Ser Thr Met Pro Phe Ile Tyr Cys
                85                  90                  95

Asn Ile Asn Glu Val Cys His Tyr Ala Arg Arg Asn Asp Lys Ser Tyr
            100                 105                 110

Trp Leu Ser Thr Thr Ala Pro Ile Pro Met Met Pro Val Ser Gln Thr
        115                 120                 125

Gln Ile Pro Gln Tyr Ile Ser Arg Cys Ser Val Cys Glu Ala Pro Ser
    130                 135                 140

Gln Ala Ile Ala Val His Ser Gln Asp Ile Thr Ile Pro Gln Cys Pro
145                 150                 155                 160

Leu Gly Trp Arg Ser Leu Trp Ile Gly Tyr Ser Phe Leu Met His Thr
                165                 170                 175

Ala Ala Gly Ala Glu Gly Gly Gly Gln Ser Leu Val Ser Pro Gly Ser
            180                 185                 190

Cys Leu Glu Asp Phe Arg Ala Thr Pro Phe Ile Glu Cys Ser Gly Ala
        195                 200                 205

Arg Gly Thr Cys His Tyr Phe Ala Asn Lys Tyr Ser Phe Trp Leu Thr
    210                 215                 220

Thr Val Glu Glu Arg Gln Gln Phe Gly Glu Leu Pro Val Ser Glu Thr
225                 230                 235                 240

Leu Lys Ala Gly Gln Leu His Thr Arg Val Ser Arg Cys Gln Val Cys
                245                 250                 255

Met Lys Ser Leu
            260

<210> SEQ ID NO 30
<211> LENGTH: 218
<212> TYPE: PRT
<213> ORGANISM: Homo sapiens

<400> SEQUENCE: 30

Gln Thr Thr Ala Ile Pro Ser Cys Pro Glu Gly Thr Val Pro Leu Tyr
```

-continued

```
1               5                   10                  15
Ser Gly Phe Ser Phe Leu Phe Val Gln Gly Asn Gln Arg Ala His Gly
            20                  25                  30

Gln Asp Leu Gly Thr Leu Gly Ser Cys Leu Gln Arg Phe Thr Thr Met
            35              40                  45

Pro Phe Leu Phe Cys Asn Val Asn Asp Val Cys Asn Phe Ala Ser Arg
        50              55                  60

Asn Asp Tyr Ser Tyr Trp Leu Ser Thr Pro Ala Leu Met Pro Met Asn
65                  70                  75                  80

Met Ala Pro Ile Thr Gly Arg Ala Leu Glu Pro Tyr Ile Ser Arg Cys
                85                  90                  95

Thr Val Cys Glu Gly Pro Ala Ile Ala Ile Ala Val His Ser Gln Thr
                100             105                 110

Thr Asp Ile Pro Pro Cys Pro His Gly Trp Ile Ser Leu Trp Lys Gly
            115                 120                 125

Phe Ser Phe Ile Met Phe Thr Ser Ala Gly Ser Glu Gly Ala Gly Gln
            130                 135                 140

Ala Leu Ala Ser Pro Gly Ser Cys Leu Glu Glu Phe Arg Ala Ser Pro
145                 150                 155                 160

Phe Leu Glu Cys His Gly Arg Gly Thr Cys Asn Tyr Tyr Ser Asn Ser
                165                 170                 175

Tyr Ser Phe Trp Leu Ala Ser Leu Asn Pro Glu Arg Met Phe Arg Lys
            180                 185                 190

Pro Ile Pro Ser Thr Val Lys Ala Gly Glu Leu Glu Lys Ile Ile Ser
            195                 200                 205

Arg Cys Gln Val Cys Met Lys Lys Arg His
            210                 215
```